US009133438B2

(12) United States Patent
Silva et al.

(10) Patent No.: US 9,133,438 B2
(45) Date of Patent: Sep. 15, 2015

(54) BROWN FAT CELL COMPOSITIONS AND METHODS

(75) Inventors: Francisco Silva, Miramar, FL (US); Mark Weinreb, Woodbury, NY (US); Amit N. Patel, Salt Lake City, UT (US); David A. Bull, Salt Lake City, UT (US)

(73) Assignee: BIORESTORATIVE THERAPIES, INC., Melville, NY (US)

( * ) Notice: Subject to any disclaimer, the term of this patent is extended or adjusted under 35 U.S.C. 154(b) by 0 days.

(21) Appl. No.: 14/129,635

(22) PCT Filed: Jun. 28, 2012

(86) PCT No.: PCT/US2012/044651
§ 371 (c)(1),
(2), (4) Date: Aug. 25, 2014

(87) PCT Pub. No.: WO2013/003595
PCT Pub. Date: Jan. 3, 2013

(65) Prior Publication Data
US 2014/0370591 A1    Dec. 18, 2014

Related U.S. Application Data

(60) Provisional application No. 61/502,508, filed on Jun. 29, 2011, provisional application No. 61/632,122, filed on Jan. 18, 2012, provisional application No. 61/632,516, filed on Jan. 25, 2012.

(51) Int. Cl.
*C12N 5/0775* (2010.01)
*C12N 5/077* (2010.01)
*A61K 35/35* (2015.01)
*G01N 33/50* (2006.01)
*A61K 35/28* (2015.01)

(52) U.S. Cl.
CPC .............. *C12N 5/0667* (2013.01); *A61K 35/35* (2013.01); *C12N 5/0653* (2013.01); *G01N 33/502* (2013.01); *G01N 33/5044* (2013.01); *A61K 35/28* (2013.01); *C12N 2500/84* (2013.01); *C12N 2500/98* (2013.01); *C12N 2501/01* (2013.01); *C12N 2501/02* (2013.01); *C12N 2501/33* (2013.01); *C12N 2501/385* (2013.01); *C12N 2501/39* (2013.01); *C12N 2501/395* (2013.01); *C12N 2506/1384* (2013.01)

(58) Field of Classification Search
CPC .................................................. C12N 5/0653
See application file for complete search history.

(56) References Cited

U.S. PATENT DOCUMENTS

| 4,832,044 | A  | 5/1989  | Garg |
| 5,145,676 | A  | 9/1992  | Fahey et al. |
| 5,165,938 | A  | 11/1992 | Knighton |
| 5,198,357 | A  | 3/1993  | Holmovist et al. |
| 5,221,253 | A  | 6/1993  | Coll |
| 5,226,914 | A  | 7/1993  | Caplan et al. |
| 5,292,330 | A  | 3/1994  | Shutt |
| 5,486,359 | A  | 1/1996  | Caplan et al. |
| 5,693,341 | A  | 12/1997 | Schroeder et al. |
| 5,736,396 | A  | 4/1998  | Bruder et al. |
| 5,749,874 | A  | 5/1998  | Schwartz |
| 5,769,899 | A  | 6/1998  | Schwartz et al. |
| 5,770,215 | A  | 6/1998  | Moshyedi |
| 5,788,713 | A  | 8/1998  | Dubach et al. |
| 5,842,477 | A  | 12/1998 | Naughton et al. |
| 5,980,504 | A  | 11/1999 | Sharkey et al. |
| 6,007,570 | A  | 12/1999 | Sharkey et al. |
| 6,073,051 | A  | 6/2000  | Sharkey et al. |
| 6,095,149 | A  | 8/2000  | Sharkey et al. |
| 6,099,514 | A  | 8/2000  | Sharkey et al. |
| 6,122,549 | A  | 9/2000  | Sharkey et al. |
| 6,126,682 | A  | 10/2000 | Sharkey et al. |
| 6,200,606 | B1 | 3/2001  | Peterson et al. |
| 6,217,527 | B1 | 4/2001  | Selmon et al. |
| 6,245,054 | B1 | 6/2001  | Fuimaono et al. |
| 6,258,086 | B1 | 7/2001  | Ashley et al. |
| 6,261,311 | B1 | 7/2001  | Sharkey et al. |
| 6,283,960 | B1 | 9/2001  | Ashley et al. |
| 6,409,727 | B1 | 6/2002  | Bales et al. |
| 6,517,568 | B1 | 2/2003  | Sharkey et al. |
| 6,530,956 | B1 | 3/2003  | Mansmann |
| 6,547,810 | B1 | 4/2003  | Sharkey et al. |
| 6,562,033 | B2 | 5/2003  | Shah et al. |
| 6,595,959 | B1 | 7/2003  | Stratienko |
| 6,604,003 | B2 | 8/2003  | Fredricks et al. |
| 6,623,733 | B1 | 9/2003  | Hossainy et al. |

(Continued)

FOREIGN PATENT DOCUMENTS

| EP | 2257176 B1 | 9/2013 |
| JP | 2010130968 | 6/2010 |

(Continued)

OTHER PUBLICATIONS

Folgiero et al (Cell Transplantation. 2010: 19(10): 1225-1235).*
Blande et al (Transfusion. Dec. 2009; 49: 2680-2685).*
Ma et al. (Biotechnology Progress. Jan./Feb. 2009. 25(1): 32-42).*
Alhadlaq et al., "Mesenchymal Stem Cells: Isolation and Therapeutics," Stem Cells and Development, 13:436-448, 2004.
Bernardo et al., "Optimization of in Vitro Expansion of Human Multipotent Mesenchymal Stromal Cells for Cell-Therapy Approaches: Further Insights in the Search for a Fetal Calf Serum Substitute," Journal of Cellular Physiology, 211:121-130, 2007.
Cannon et al., "Cultures of Adipose Precursor Celis from Brown Adipose Tissue and of Clonal Brown-Adipocyte-Like Cell Lines," Methods in Molecular Biology, 155:213-224, 2001.
Caplan, "Mesenchymal Stem Cells," Journal of Orthopaedic Research, 9:641-650, 1991.

(Continued)

*Primary Examiner* — Scott Long
(74) *Attorney, Agent, or Firm* — K&L Gates LLP

(57) ABSTRACT

Methods of developing and using cell lines, such as stem cell lines, for therapeutic or cosmetic use. In one embodiment the cell lines are used to treat a wide range of degenerative and metabolic disorders including, but not limited to, obesity, diabetes, hypertension, and cardiac deficiency. Also described are methods of using such cell lines to screen for compounds that play a role in regulating a variety of processes.

16 Claims, 17 Drawing Sheets

(56) References Cited

U.S. PATENT DOCUMENTS

| | | | |
|---|---|---|---|
| 6,638,276 B2 | 10/2003 | Sharkey et al. |
| 6,699,471 B2 | 3/2004 | Radice et al. |
| 6,699,484 B2 | 3/2004 | Whitmore et al. |
| 6,726,685 B2 | 4/2004 | To et al. |
| 6,733,496 B2 | 5/2004 | Sharkey et al. |
| 6,821,276 B2 | 11/2004 | Lambrecht et al. |
| 6,832,997 B2 | 12/2004 | Uchida et al. |
| 6,835,377 B2 | 12/2004 | Goldberg et al. |
| 6,872,567 B2 | 3/2005 | Thomas et al. |
| 7,069,087 B2 | 6/2006 | Sharkey et al. |
| 7,229,959 B1 | 6/2007 | Drohan et al. |
| 7,273,756 B2 | 9/2007 | Adkisson et al. |
| 7,322,962 B2 | 1/2008 | Forrest |
| 7,618,662 B2 | 11/2009 | Hines et al. |
| 7,824,711 B2 | 11/2010 | Kizer et al. |
| 7,896,909 B2 | 3/2011 | Sharkey et al. |
| 7,905,863 B1 | 3/2011 | Forrest |
| 8,017,394 B2 | 9/2011 | Adkisson, IV et al. |
| 8,052,661 B2 | 11/2011 | McGuckin et al. |
| 8,192,759 B2 | 6/2012 | Seyedin et al. |
| 8,672,920 B2 | 3/2014 | Makower et al. |
| 2001/0031963 A1 | 10/2001 | Sharkey et al. |
| 2002/0022830 A1 | 2/2002 | Sharkey et al. |
| 2003/0050709 A1 | 3/2003 | North et al. |
| 2003/0181964 A1 | 9/2003 | Sharkey et al. |
| 2003/0224411 A1 | 12/2003 | Stanton et al. |
| 2003/0225331 A1 | 12/2003 | Diederich et al. |
| 2004/0015215 A1 | 1/2004 | Fredricks et al. |
| 2004/0015218 A1 | 1/2004 | Finch et al. |
| 2004/0078077 A1 | 4/2004 | Binette et al. |
| 2004/0083002 A1 | 4/2004 | Belef et al. |
| 2004/0087994 A1 | 5/2004 | Suddaby |
| 2004/0102824 A1 | 5/2004 | Sharkey et al. |
| 2004/0111136 A1 | 6/2004 | Sharkey et al. |
| 2004/0111137 A1 | 6/2004 | Shankey et al. |
| 2004/0127963 A1 | 7/2004 | Uchida et al. |
| 2004/0136968 A1 | 7/2004 | Zheng et al. |
| 2004/0193045 A1 | 9/2004 | Scarborough et al. |
| 2004/0229786 A1 | 11/2004 | Attawia et al. |
| 2004/0229878 A1 | 11/2004 | DiMauro et al. |
| 2004/0235166 A1 | 11/2004 | Prockop et al. |
| 2005/0019865 A1 | 1/2005 | Kihm et al. |
| 2005/0038520 A1 | 2/2005 | Binette et al. |
| 2005/0100536 A1 | 5/2005 | Mishra |
| 2005/0118230 A1 | 6/2005 | Hill et al. |
| 2005/0124038 A1 | 6/2005 | Aguiar et al. |
| 2005/0196387 A1 | 9/2005 | Seyedin et al. |
| 2005/0205498 A1 | 9/2005 | Sowemimo-Coker et al. |
| 2005/0276792 A1 | 12/2005 | Kaminski et al. |
| 2006/0073124 A1 | 4/2006 | Garcia Castro et al. |
| 2006/0128016 A1 | 6/2006 | Tokushima et al. |
| 2006/0228391 A1 | 10/2006 | Seyedin et al. |
| 2006/0251631 A1 | 11/2006 | Adkisson, IV et al. |
| 2006/0275273 A1 | 12/2006 | Seyedin et al. |
| 2007/0087032 A1 | 4/2007 | Chang et al. |
| 2007/0122904 A1 | 5/2007 | Nordon |
| 2007/0128155 A1 | 6/2007 | Seyedin et al. |
| 2007/0128722 A1 | 6/2007 | Lin et al. |
| 2008/0038233 A1 | 2/2008 | Freemont et al. |
| 2008/0220101 A1 | 9/2008 | Buchwald-Werner |
| 2008/0248003 A1 | 10/2008 | Katz et al. |
| 2008/0299214 A1 | 12/2008 | Seyedin et al. |
| 2009/0010896 A1 | 1/2009 | Centeno et al. |
| 2009/0012629 A1 | 1/2009 | Yao et al. |
| 2009/0143867 A1 | 6/2009 | Gage et al. |
| 2009/0175927 A1 | 7/2009 | Gammelsaeter et al. |
| 2009/0208464 A1 | 8/2009 | Centeno |
| 2009/0214491 A1 | 8/2009 | Burt |
| 2009/0249511 A1 | 10/2009 | Krishnapuram et al. |
| 2009/0274665 A1 | 11/2009 | Akabuto et al. |
| 2009/0304643 A1 | 12/2009 | Khurgel et al. |
| 2010/0150885 A1 | 6/2010 | Tseng et al. |
| 2010/0168022 A1 | 7/2010 | Centeno |
| 2010/0272662 A1 | 10/2010 | Bonte et al. |
| 2010/0322994 A1 | 12/2010 | Kizer et al. |
| 2011/0052533 A1 | 3/2011 | Centeno |
| 2011/0054929 A1 | 3/2011 | Centeno |
| 2011/0117066 A1 | 5/2011 | Ailhaud et al. |
| 2011/0200642 A1 | 8/2011 | Centeno |
| 2011/0245804 A1 | 10/2011 | Centeno |
| 2011/0256095 A1 | 10/2011 | Seyedin et al. |
| 2011/0276001 A1 | 11/2011 | Centeno et al. |
| 2012/0009224 A1 | 1/2012 | Kizer et al. |
| 2012/0009270 A1 | 1/2012 | Kizer et al. |
| 2012/0087948 A1 | 4/2012 | Kizer et al. |
| 2012/0107384 A1 | 5/2012 | Yao et al. |
| 2013/0074199 A1 | 3/2013 | Spiegelman et al. |
| 2013/0084341 A1 | 4/2013 | Centeno |
| 2013/0108593 A1 | 5/2013 | Centeno |
| 2014/0017789 A1 | 1/2014 | Silva et al. |
| 2014/0023622 A1 | 1/2014 | Silva et al. |
| 2014/0038177 A1 | 2/2014 | Silva et al. |
| 2014/0212875 A1 | 7/2014 | Silva et al. |

FOREIGN PATENT DOCUMENTS

| | | |
|---|---|---|
| KR | 2003 0024028 | 3/2003 |
| WO | WO 97/34614 A1 | 9/1997 |
| WO | WO 98/51317 A1 | 11/1998 |
| WO | WO 01/80865 A2 | 11/2001 |
| WO | WO 2004/067704 A2 | 8/2004 |
| WO | WO 2005/046761 A1 | 5/2005 |
| WO | WO 2005/085421 A2 | 9/2005 |
| WO | WO 2007/087519 A2 | 8/2007 |
| WO | 2008/034803 | 3/2008 |
| WO | 2009/006161 | 1/2009 |
| WO | WO 2009/085969 A2 | 7/2009 |
| WO | WO 2009/114785 A2 | 9/2009 |
| WO | 2009/137613 | 11/2009 |
| WO | WO 2009/156413 A1 | 12/2009 |
| WO | WO 2010/065854 A1 | 6/2010 |

OTHER PUBLICATIONS

Caplan et al., "Mesenchymal stem cells: building blocks for molecular medicine in the 21st century," Trends in Molecular Medicine, 7(6):259-264, Jun. 2001.

Casteilla et al., "Differentiation of ovine brown adipocyte precursor cells in a chemically defined serum-free medium," European Journal of Biochemistry, 198(1):195-'99, 1991.

Cigolini et al., "Human Brown Adipose Cells in Culture," Experimental Cell Research, 159(1):261-266, 1985.

Deschaseaux et al., "Direct selection of human bone marrow mesenchymal stem cells using an anti-CD49a antibody reveals their $CD45^{med.low}$ phenotype," British Journal of Haematology, 122:506-517, 2003.

Doucet et al., "Platelet Lysates Promote Mesenchymal Stem Cell Expansion: A Safety Substitute for Animal Serum in Cell-Based Therapy Applications," Journal of Cellular Pysiology, 205:228-236, 2005.

Fortier et al., "Isolation and chondrocytic differentiation of equine bone marrow-derived mesenchymal stem cells," AJVR, 59(9):1182-1187, Sep. 1998.

Huss, "Perspectives on the Morphology and Biology of CD34-Negative Stem Cells," Journal of Hematotherapy & Stem Cell Research, 9:783-793, 2000.

Kang et al., "Role of c-Jun N-terminal Kinase in the PDGF-Induced Proliferation and Migration of Human Adipose Tissue-Derived Mesenchymal Stem Cells," Journal of Cellular Biochemistry, 95:1135-1145, 2005.

Kim et al., "Role of CD9 in proliferation and proangiongenic action of human adipose-derived mesenchymal stem cells," Pflügers Archiv—European Journal of Physiology, 455:283-296, 2007.

Lange et al., "Accelerated and Safe Expansion of Human Mesenchymal Stromal Cells in Animal Serum-Free Medium for Transplantation and Regenerative Medicine," J. Cell. Physiol. 213:18-26, 2007.

Lee et al., "Inducible Brown Adipogenesis of Supraclaicular Fat in Adult Humans," Endocrinology, 152(10):3597-3602, Oct. 2011.

Müller et al., "Animal serum-free culture conditions for isolation and expansion of multipotent mesenchymal stromal cells from human BM," Cytotherapy 8(5):437-444, 2006.

(56) References Cited

OTHER PUBLICATIONS

Niemeyer et al., "Comparison of Immunological properties of Bone Marrow Stromal Cells and Adipose Tissue-Derived Stem Cells Before and After Osteogenic Differentiation in Vitro," Tissue Engineering, 13(1):111-121, 2007.
Sato et al., "Reversible Expression of CD34 by Murine Hematopoietic Stem Cells," Blood, 94:2548-2554, 1999.
Schallmoser et al., "Human platelet lysate can replace fetal bovine serum for clinical-scale expansion of functional mesenchymal stromal cells," Transfusion, 47:1436-1446, 2007.
Tapp et al., "Adiose-Derived Stem Cells: Characterization and Current Application in Orthopaedic Tissue Repair," Experimental Biology and Medicine 234:1-9, 2009.
Tondreau et al., "Isolation of BM mesenchymal stem cells by plastic adhesion or negative selection: phenotype, proliferation kinetics and differentiation potential," Cytotherapy, 6(4):372-379, 2004.
Tran et al., "Transplantation of adipose tissue and stem cells: role in metabolism and disease," Nature Reviews/Endocrinology, 6(4):195-213, Apr. 2010.
International Search Report and the Written Opinion of the International Searching Authority for PCT/US2012/044651, mailed Nov. 9, 2012, 35 pages.
Acosta et al., "The Potential Role of Mesenchymal Stem Cell Therapy for Intervertebral Disc Degeneration: A Critical Overview", Neurosurg. Focus 2005, 19(3):E4.
Ahuja et al., "Identification of Two Subpopulations of Rat Monocytes Expressing Disparate Molecular Forms and Quantities of CD43", Cell Immunol., 1995, 163(1):59-69.
Ando et al., "Cartilage repair using an in vitro generated scaffold-free tissue-engineered construct derived from porcine synovial mesenchymal stem cells", Biomaterials 1-9. Available Website: www.sciencedirect.com (2007).
Anitua et al., "Autologous Platelets as a Source of Proteins for Healing and Tissue Regeneration", Thromb. Haemost., 2004, 91:4-15.
Avascular Necrosis in patient education of Illinois Bone and Joint Institute, 2003 downloaded from the hipdoc.com/avas.htm. p. 1-2.
Baecher-Allan et al., "Functional Analysis of Highly Defined, FACS-Isolated Populations of Human Regulatory CD4+CD25+ T Cells", Clinical Immunology, 2005, 115:10-18.
Barry, "Mesenchymal Stem Cell Therapy in Joint Disease", Novartis Found. Symp., 2003, 249:86-102, 170-4, 239-41.
Bensaid et al., "A Biodegradable Fibrin Scaffold for Mesenchymal Stem Cell Transplantation", Biomaterials, 24:2497-2502.
Billard et al., "Switch in the Protein Tyrosine Phosphatase Associated with Human CD100 Semaphorin at Terminal B-Cell Differentiation Stage", Blood, 2000, 95(3):965-972.
Bircher et al., "Discitis Following Lumbar Surgery", Spine, 1988, 13(1):98-102.
Borner et al., "Antibiotic Therapy and Long-Term Outcome in Patients with Vertebral Osteomyelitis", Schweiz Med. Wochenschr. 1989, 119(1): 19-21 (German, English Abstract Only).
Brisby et al., "Cell Therapy for Disc Degeneration—Potentials and Pitfalls", Orthop. Clin. North Am., 2004, 35(1):85-93.
Buckwalter et al., "Articular Cartilage: Degeneration and Osteoarthritis, Repair, Regeneration, and Transplantation", AAOS Instr. Course Lect., 1998, 47:487-504.
Buhring et al., "The Monoclonal Antibody 97 A6 Defines a Novel Surface Antigen Expressed on Human Basophils and Their Multipotent and Unipotent Progenitors", Blood, 1999, 94(7):2343-2356.
Caligiuri et al., "Functional Consequences of Interleukin 2 Receptor Expression on Resting Human Lymphocytes. Identification of a Novel Natural Killer Cell Subset with High Affinity Receptors", J. Exp. Med., 1990, 171:1509-1526.
Cashman et al., "Mechanisms that Regulate the Cell Cycle Status of Very Primitive Hematopoietic Cells in Long-Term Human Marrow Cultures. I. Stimulatory Role of a Variety of Mesenchymal Cell Activators and Inhibitory Role of TGF-Beta", Blood, 1990, 75(1):96-101.
Cassiede et al., "Osteochondrogenic Potential of Marrow Mesenchymal Progenitor Cells Exposed to TGF-β1 or PDGF-BB as Assayed in Vivo and in Vitro", J. of Bone and Miner. Res., 1996, 11(9):1264-1273.
Castro et al., "Failure of Bone Marrow Cells to Transdifferentiate into Neutral Cells in Vivo", Science, (2002), 297:1299.
Centeno et al., "Partial Regeneration of the Human Hip Nucleated Cell Transfer: A Case Study", Pain Physician, 2006, 9:253-256.
Centeno et al., "Increased Knee Cartilage Volume in Degenerative Joint Disease using Percutaneously Implanted, Autologous Mesenchymal Stem Cells, Platelet Lysate and Dexamethasone", The American Journal of Case Reports, (2008) 9:201-206.
Centeno et al., "Increased Knee Cartilage Volume in Degenerative Joint Disease using Percutaneously Implanted, Autologous Mesenchymal Stem Cells", Pain Physician, (2008) 11(3):343-353.
Centeno et al., "A Case Series of Percutaneous Treatment of Non-Union Fractures with Aulogous, Culture Expanded, Bone Marrow Derived, Mesenchymal Stem Cells and Platelet Lysate", Bioengineering & Biomedical Science, 2011, S2:007.
Centeno et al., "Regeneration of meniscus cartilage in a knee treated with percutaneously implanted autologous mesenchymal stem cells", Medical Hypotheses, 2008, 71:900-908.
Centeno et al., "The Use of Mesenchymal Stem Cells in Orthopedics" Stem Cells and Cancer Stem Cells, 2012, 1:173-179.
Charalambous et al., "Septic Arthritis Following Intra-Articular Steroid Injection of the Knee—a Survey of Current Practice Regarding Antiseptic Technique used During Intra-Articular Steroid Injection of the Knee", Clin. Rheumatol., 2003, 22:386-390.
Chazerain et al., "Septic Hip Arthritis After Multiple Injections into the Joint of Hyaluronate and Glucocorticoid", Rev. Rhum. Engl. Ed., 1999, 66(7-9):436-437.
D'Ippolito et al., "Age-Related Osteogenic Potential of Mesenchymal Stromal Stem Cells from Human Verterbral Bone Marrow", J. Bone Miner. Res., 1999, 14(7):1115-122.
Dall et al., "Postoperative Discitis. Diagnosis and Management", Clin. Orthop. Relat. Res., 1987, 224:138-146.
Del Curling et al., "Changing Concepts in Spinal Epidural Abscess: A Report of 29 Cases", Neurosurgery, 1990, 27(2):185-192.
Elghetany et al., "Assessment of CD24 Expression on Bone Marrow Neutrophilic Granulocytes: CD24 is a Marker for the Myelocytic Stage of Development", Am. J. Hematol., 2002, 71:348-349.
Fang et al., "Biocompatibility Studies on Fibrin Glue Cultured with Bone Marrow Mesenchymal Stem Cells in Vitro", J. of Huazhong. Univ. of Sci. Technolog. Med. Sci., 2004, 24(3):272-274.
Fiedler et al., "BMP-2, BMP-4, and PDGF-bb Stimulate Chemotactic Migration of Primary Human Mesenchymal Progenitor Cells", J. Cell. Biochem., 2002, 87:305-312.
Fiedler et al., "To Go or Not to Go: Migration of Human Mesenchymal Progenitor Cells Stimulated by Isoforms of PDGF", J. Cell. Biochem., 2004, 93:990-998.
Fraser et al., "Each Hypersensitive Site of the Human Beta-Globin Locus Control Region Confers a Different Developmental Pattern of Expression on the Globin Genes", Genes & Development, 1993, 7:106-113.
Fujiwara et al., "Acute Purulent Discitis with Epidural Abscess of the Cervical Spine in an Adult", Neurol. Med. Chir., (Tokyo), 1994, 34(6):382-384.
Gajdusek et al., "Basic Fibroblast Growth Factor and Transforming Growth Factor Beta-1: Synergistic Mediators of Angiogenesis in Vitro", J. Cell. Physiol., (1993) 157(1):133-144.
Gazzit et al., "Purified CD34+ Lin-Thy+ Stem Cells do Not Contain Clonal Myeloma Cells", Blood, 1995, 86(1):381-389.
Gibson et al., "Surgery for Degenerative Lumbar Spondylosis: Updated Cochrane Review", 2005, Spine, 30(20):2312-2320.
Gruber et al., "Recent Advances in Disc Cell Biology", 2003, Spine, 28(2): 186-193.
Gruber et al., "Platelet-Released Supernatants Increase Migration and Proliferation, and Decrease Osteogenic Differentiation of Bone Marrow-Derived Mesenchymal Progenitor Cells Under in Vitro Conditions", Platelets, 2004, 15(1):29-35.
Gustafson et al., "Further Investigations into the Potentiation of Infection by Intra-Articular Injection of Polysulfated

(56) References Cited

OTHER PUBLICATIONS

Glycosaminoglycan and the Effect of Filtration and Intra-Articular Injection of Amikacin", Am. J. Vet. Res., 1989, 50(12):2018-2022.
Hickstein et al., "Identification of the Promoter of the Myelomonocytic Leukocyte Integrin CDllb", Proc. Natl. Acad. Sci., USA, 1992, 89(6):2105-2109.
Hip Replacement Surgery. John Hopkins Medicine. Downloaded on Jul. 14, 2012 from www.hopkinsmedicine.org/healthlibrary/conditions/adult/orthopaedic_disorders/hip_replacement_surger_85, P01372. p. 1-4.
Hirschi et al., "Endothelial Cells Modulate the Proliferation of Mural Cell Precursors via Platelet-Derived Growth Factor-BB and Heterotypic Cell Contact", Circ. Res., 1999, 84(3):298-305.
Hoelscher et al., "Effects of Very High Antibiotic Concentrations on Human Intervertebral Disc Cell Proliferation, Viability, and Metabolism in Vitro", Spine, 2000, 25(15): 1871-1877.
Huang et al., "Formation of Haematopoietic Microenvironment and Haematopoietic Stem Cells from Single Human Bone Marrow Stem Cells", 1994, Nature, 368(6472):664.
Iversen et al., "Prognosis in Postoperative Discitis, A Retrospective Study of 111 Cases", Acta Orthop. Scand., 1992, 63(3):305-309.
Johnstone et al., "Autologous Mesenchymal Progenitor Cells in Articular Cartilage Repair", Clin. Orthop. Relat. Res., 1999, 367 Suppl:S156-162.
Kambin et al., "Percutaneous Lumbar Discectomy Review of 100 Patients and Current Practice", Clin. Orthop. Relat. Res., 1989, 238:24-34.
Kaps et al., "Human Platelet Supernatant Promotes Proliferation but Not Differentiation of Articular Chondrocytes", Med. Biol. Eng. Comput., 2002, 40(4):485-490.
Katz et al., "Effect of Platelet-Derived Growth Factor on Enriched Populations of Haemopoietic Progenitors from Patients with Chronic Myeloid Leukaemia", Leuk. Res., 1987, 11(4):339-344.
Kilian et al., "Effects of Platelet Growth Factors on Human Mesenchymal Stem Cells and Human Endothelial Cells in Vitro", Eur. J. Med. Res., 2004, 9(7):337-344.
Kirshenbaum et al., "Demonstration that Human Mast Cells Arise from a Progenitor Cell Population that is CD34+, c-kit+, and Expresses Aminopeptidase N (CD13)", Blood, 1999, 94:2333-2342.
Kitoh et al., "Transplantation of Marrow-Derived Mesenchymal Stem Cells and Platelet-Rich Plasma During Distraction Osteogenesis—a Preliminary Result of Three Cases", Bone, 2004, 35:892-898.
Koga et al., "Local adherent technique for transplanting mesenchymal stem cells as a potential treatment of cartilage defect", Arthritis Research & Therapy, 2008, 10(R84), 1-10. Available web site: http://arthritis-research.com/content/10/4/R84 (Adherent Technique).
Koga et al., "Local adherent technique for transplanting mesenchymal stem cells as a potential treatment of cartilage defect", Arthritis Research & Therapy, 2008, 10(R84), 1-10. Available web site: http://arthritis-research.com/content/10/4/R84 (Novel Technique).
Koh et al., "Co-Culture of Human CD34+ Cells with Mesenchymal Stem Cells Increases the Survival of CD34+ Cells Against the 5-Aza-Deoxycytidine- or Trichostatin A-Induced Cell Death", Biochem. Biophys. Res. Commun., 2005, 329:1039-1045.
Kortelainen et al., "Fatal Complications of Intramuscular and Intra-Articular Injections" Z Rechtsmed., 1990, 103:547-554.
Kravitz et al. "How Do Muscles Grow", IDEA Fitness Journal; 3(2), 23-25 (2006) (http://www.unm.eduf kravi tz/ Article% 20folder/muscles growLK.html).
Laiho et al., "Septic Arthritis Due to Prevotella Bivia After Intra-Articular Hip Joint Injection", Joint Bone Spine, 2001, 68:443-444.
Luyten, "Mesenchymal Stem Cells in Osteoarthritis", Curr. Opin. Rheumatol., 2004, 16:599-603.
Magne et al., "Mesenchymal Stem Cell Therapy to Rebuild Cartilage", Trends Mol. Med., 2005, 11(11):519-526.
Martineau et al., "Effects of Calcium and Thrombin on Growth Factor Release from Platelet Concentrates: Kinetics and Regulation of Endothelial Cell Proliferation", Biomaterials, 2004, 25:4489-4502.
Medina et al., "Purification of Human Tonsil Plasma Cells: Pre-Enrichment Step by Immunomagnetic Selection of CD3l +Cells", Cytometry, 2000, 39(3):231-234.
Mezey et al., "Comment on and Response to Comment on Failure of Bone Marrow Cells to Transdifferentiate into Neutral Cells in Vivo", Science, 2003, 299: 1184b-1184c.
Miyata et al., "Platelet-Derived Growth Factor-BE (PDGF-BB) Induces Differentiation of Bone Marrow Endothelial Progenitor Cell-Derived Cell Line TR-BME2 into Mural Cells, and Changes the Phenotype", J. Cell. Physiol., 2005, 204:948-955.
Morshed et al., "Septic Arthritis of the Hip and Intrapelvic Abscess Following Intra-Articular Injection of Hylan G-F 20. A Case Report", J. Bone Joint Surg. Am., 2004, 86:823-826.
Munirah et al., "Autologous Versus Pooled Human Serum for Articular Chondrocyte Growth", Journal of Orthopedic Surgery, 2008, 16(2):220-229.
Murphy et al., "Stem Cell Therapy in a Caprine Model of Osteoarthritis", 2003, Arthritis Rheum., 2003, 48(12):3464-3474.
Murray et al., "CD 109 is Expressed on a Subpopulation of CD34 + Cells Enriched in Hematopoietic Stem and Progenitor Cells", 1999, Exp. Hematol., 27: 1282-1294.
Nakayama et al., "Evaluation of Glycosaminoglycans Levels in Normal Joint Fluid of the Knee", J. Nippon Med. Sch., 2000, 67(2)92-95.
Nielsen et al., "Postoperative Discitis. Radiology of Progress and Healing", Acta Radiol., 1990, 31 (6):559-563.
Olweus et al., "CD64/Fc Gamma RI is a Granulo-Monocytic Lineage Marker on CD34+ Hematopoietic Progenitor Cells", 1995, Blood, 85(9):2402-2413.
Onofrio, "Intervertebral Discitis: Incidence, Diagnosis, and Management", Clin. Neurosurg., 1980, 27:481-516.
Ordog et al., "Purification of Interstitial Cells of Cajal by Fluorescence-Activated Cell Sorting", Am. J. Physiol. Cell Physiol, 2004, 286(2):448-456.
Orpen et al., "Delayed Presentation of Septic Arthritis of a Lumbar Facet Joint after Diagnostic Facet Joint Injection", J. Spinal Disord. Tech., 2003, 16(3):285-287.
Oshima et al., "Fate of Transplanted Bone-Marrow-Derived Mesenchymal Cells During Osteochondral Repair using Transgenic Rats to Simulate Autologous Transplantation", OsteoArthritis Cartilage, 2004, 12:811-817.
Otawa et al., "Comparative Multi-Color Flow Cytometric Analysis of Cell Surface Antigens in Bone Marrow Hematopoietic Progenitors Between Refractory Anemia and Aplastic Anemia", Leukemia Research, 2000, 24:359-366.
Park et al., "Thoughts and Progress, Tissue-Engineered Cartilage Using Fibrin/Hyaluronan Composite Gel and its in Vivo Implantation", Artif. Organs, 2005, 29(10):838-860.
Pellaton et al., "Spectic Arthritis Following Repeated Intraarticular Injections of Glycosaminoglycanpolysulfat (Arteparon®) and Steroids for Osteoarthrosis of the Knee Joint", (French,English Abstract Only) Schweiz. Rudnsch. Med. Prax., 1981, 70(52):2364-2367.
Pietramaggiori et al., "Freeze-Derived Platelet-Rich Plasma Shows Beneficial Healing Properties in Chronic Wounds", Wound Rep. Reg., 2006, 14:573-580.
Ponte et al., "Septic Discitis Resulting from *Escherichia coli* Urosepsis", J. Fam. Pract., 1992, 34(6):767-771.
Prins et al., "Effect of Purified Growth Factors on Rabbit Articular Chondrocytes in Monolayer Culture. II. Sulfated Proteoglycan Synthesis" Arthritis & Rheumatism, 1982, 25(10):1228-1238.
Rasmusson et al., "Mesenchymal Stem Cells Inhibit the Formation of Cytotoxic T Lymphocytes, but Not Activated Cytotoxic T Lymphocytes or Natural Killer Cells", Transplantation, 2003, 76(8):1208-1213.
Reddi et al., "Bone Induction by Osteogenin and Bone Morphogenetic Proteins", Biomaterials, 1990, 11:33-34.
Regenexx™ PR article, published Nov. 8, 2007; downloaded May 14, 2012.
Richardson et al., "Intervertebral Disc Cell-Mediated Mesenchymal Stem Cell Differentiation", Stem Cells, 2006, 24:707-716.

(56) References Cited

OTHER PUBLICATIONS

Ries et al., "MMP-2, MTI-MMP, and TIMP-2 are essential for the invasive capacity of human mesenchymal stem cells: differential regulation by inflammatory cytokines", (2007) Blood 109(9):4055-4063.
Roberts et al., "Autologous Chondrocyte Implantation for Cartilage Repair: Monitoring its Success by Magnetic Resonance Imaging and Histology", Arthritis Research and Therapy, 2003, 5(1):R60-R73.
Rolf et al., "Intra-Articular Absorption and Distribution of Ketoprofen After Topical Plaster Application and Oral Intake in 100 Patients Undergoing Knee Arthroscopy", Rheumatology, 1999, 38:564-567.
Ruszymah, "Autologous Human Fibrin as the Biomaterial for Tissue Engineering", Med. J. Malaysia, 2004, 59 Suppl. B:30-1.
Sah et al., "Effects of Fibrin Glue Components on Chondrocyte Growth and Matrix Formation," in 49th Annual Meeting of the Orthopaedic Research Society, 2003, poster #0721, pp. 1-2.
Sanchez et al., "Is Platelet-Rich Plasma the Perfect Enhancement Factor? A Current Review", Int. J. Oral Maxillofac., Implants, 2003, 18:93-103.
Silverman et al., "Injectable Tissue-Engineered Cartilage Using a Fibrin Glue Polymer", Plast. Reconstr. Surg., Jun. 1999,103(7):1809-1818.
Simmons et al., "CD34 Expression by Stromal Precursors in Normal Human Adult Bone Marrow", Blood, 1991, 78(11):2848-2853.
Singer et al., "Simian Virus 40-Transformed Adherent Cells From Human Long-Term Marrow Cultures: Cloned Cell Lines Produce Cells with Stromal and Hematopoietic Characteristics", Blood, 1987, 70(2):464-474.
Singer et al., "Evidence for a Stem Cell Common to Hematopoiesis and its in Vitro Microenvironment: Studies of Patients with Clonal Hematopoietic Neoplasia", Leuk. Res., 1984, 8(4):535-545.
Solchaga et al., "Treatment of Osteochondral Defects with Autologous Bone Marrow in a Hyaluronan-Based Delivery Vehicle", Tissue Engineering, (2002) vol. 8, No. 2, pp. 333-347.
Spaggiari et al., "Mesenchymal Stem Cell-Natural Killer Cell Interactions: Evidence that Activated NK Cells are Capable of Killing MSCs, Whereas MSCs can Inhibit IL-2-Induced NK-Cell Proliferation", Blood, 2006, 107(4):1484-1490.
Stacey et al., "Randomised Double-Blind Placebo Controlled Trial of Topical Autologous Platelet Lysate in Venous Ulcer Healing", Eur. J. Vase. Endovasc. Surg., 2000, 20:296-301.
Terstappen et al., "Sequential Generations of Hematopoietic Colonies Derived From Single Nonlineage-Committed CD34+CD38-Progenitor Cells", Blood,1991, 77(6): 1218-1227.
Toba et al., "Novel Technique for the Direct Flow Cytofluorometric Analysis of Human Basophils in Unseparated Blood and Bone Marrow, and the Characterization of Phenotype and Peroxidase of Human Basophils", Cytometry, 1999, 35(3):249-259.
Tosh et al., "Conversion of Pancreatic Cells to Hepatocytes", Biochem. Soc. Trans., 2002, 30:51-55.
Ueda et al., "Induction of Senile Osteoporosis in Normal. Mice by Intra-Bone Marrow-Bone Marrow Transplantation from Osteoporosis-Prone Mice", Stem Cells, 2007, 25(6): 1356-1363.
Weber, "Infectious Damage to the Intervertebral Disk-Before and Following Discotomy", Z. Orthop Ihre Grenzeb, 1988, 126(5):555-562 (German, English Abstract Only).
Willems et al., "Lumbar Discography: Should we Use Prophylactic Antibiotics? A Study of 435 Consecutive Discograms and a Systematic Review of the Literature", J. Spinal Disord. Tech., Jun. 2004, 17(3)243-247.
Willheim et al., "Purification of Human Basophils and Mast Cells by Multistep Separation Technique and mAb to CDwl7 and CD117/c-kit", J. Immunological Methods, 1995, 182:115-129.
Xaymardan et al., "Platelet-Derived Growth Factor-AB Promotes the Generation of Adult Bone Marrow-Derived Cardiac Myocytes", Circ Res., 94(5):E39-E45.
Xian et al., "Repair of Injured Articular and Growth Plate Cartilage Using Mesenchymal Stem Cells and Chondrogenic Gene Therapy", Current Stem Cells Research and Therapy, (2006) 1:213-229.

Yamada et al., "Bone Regeneration Following Injection of Mesenchymal Stem Cells and Fibrin Glue with a Biodegradable Scaffold", J. Cranio-Maxillofac. Surg., 2003, 31:27-33.
Yang et al., "Cardioprotective Effects of Platelets Against Ischaemia-Reperfusion Injury are Related in Part to Platelet Glutathione Redox Cycle", Cardiovasc. Res., (1994) 28(10):1586-1593. Abstract.
Ye et al., "Effect of Three Growth Factors on Proliferation and Cell Phenotype of Human Fetal Meniscal Cells" Chinese Journal Reconstructive Surgery, (2007) 21 (I 0): 1137-1138 with English Abstract.
Zhu et al., "Recombinant Human Acidic Fibroblast Growth Factor Accelerates the Healing of Full Thickness Dermal Wounds in Pigs", Modern Rehabilitation, (2001) 5(9):31 with English Abstract.
Zhu et al., "Hypoxia and Serum Deprivation-Induced Apoptosis in Mesenchymal Stem Cells", Stem Cells, 2006, 24:416-425.
Ahfeldt, T. et al., "Programming human pluripotent stem cells into white and brown adipocytes", Nature Cell Biol., vol. 14, No. 2, 209-219, Feb. 2012.
Blande et al., "Adipose tissue mesenchymal stem cell expansion in animal serum-free medium supplemented with autologous human platelet lysate", Transfusion 49: 2680-5, 2009.
Bukowiecki et al., "Proliferation and differentiation of brown adipocytes from interstitial cells during cold acclimation", American Journal of Physiology 250, C880-C887, 1986.
Cannon et al., "Brown Adipose Tissue: Function and Physiological Significance", Physiol. Rev. 84:277-359, 2004.
Crisostomo et al., "High Passage Number of Stem Cells Adversely Affects Stem Cell Activation and Myocardial Protection," Shock, 26(6):575-580, 2006.
Cypress et al., "Identification and Importance of Brown Adipose Tissue in Adult Humans", New England Journal of Medicine, 360:1509-1517, 2009.
Freshney, Culture of Animal Cells, A Manual of Basic Technique, Third edition, Wiley-Liss, New York, 1994.
EMBL sequence data bank accession No. X56545.1, NCBI BLAST search performed Jun. 9, 2014 from NCBI website.
Hauner et al., "Promoting effect of glucocorticoids on the differentiation of human adipocyte precursor cells cultured in a chemically defined medium", J. Clin. Invest., vol. 84, Nov. 1989, pp. 1663-1670.
Hernandez, et al., "Dexamethasone Inhibits Growth Factor-Induced Type 3 Deiodenase Activity and mRNA Expression in a Cultured Cell Line Derived from Rat Neonatal Brown Fat Vascular-Stromal Cells", Endocrinology 143 (7), pp. 2652-2658, Jul. 1, 2002.
Kajimura et al., "Initiation of myoblast to brown fat switch by a PRDM16-C/EBP-β transcriptional complex", Nature, vol. 460, 1154-1158, Aug. 2009.
Kajimura et al., "Transcriptional control of brown fat development", Cell Metabolism, 11(4): 257-262, Apr. 2010.
Klein et al., "Novel adipocyte lines from brown fat: a model system for the study of differentiation, energy metabolism, and insulin action", BioEssays vol. 24, pp. 382-388, Wiley Periodicals, Inc., Jan. 1, 2002.
Klein et al., "β3-Adrenergic Stimulation Differentially Inhibits Insulin Signaling and Decreases Insulin-induced Glucose Uptake in Brown Adipocytes", The Journal of Biological Chemistry, vol. 274, No. 49, Dec. 3, 1999, 34795-34802.
Lean, M. E. J., "Brown Adipose Tissue in Man," Proceedings of the Nutrition Society, 1989, 48: 243-256.
Nedergaard et al., "Unexpected evidence for active brown adipose tissue in adult humans", Am J Physiol Endocrinol Metab 293: E444-E452, 2007, May 1, 2007.
Patel, et al., "Putative Population of Adipose-Derived Stem Cells Isolated from Mediastinal Tissue During Cardiac Surgery", Cell Transplantation, vol. 22, pp. 507-511, 2013.
Riordan et al., "Non-expanded adipose stromal vascular fraction cell therapy for multiple sclerosis", Journal of Translational Medicine, 7(29): 1-9, 2009.
Rousseau et al., "Brown fat in breast cancer patients: analysis of serial (18)F-FDG PET/CT scans", European Journal of Nuclear Medicine and Molecular Imaging, Jul. 2006, vol. 33, No. 7: 785-791.

(56) References Cited

OTHER PUBLICATIONS

Silva, et al., "Metabolically Active Human Brown Adipose Tissue Derived Stem Cells", Stem Cells. vol. 32, No. 2, pp. 572-581, Feb. 13, 2014.

Schulz et al., "Identification of inducible brown adipocyte progenitors residing in skeletal muscle and white fat", Proceedings of the National Academy of Sciences, vol. 108, No. 1, pp. 143-148, Jan. 4, 2011.

Seale et al., "Transcriptional control of brown fat determination by PRDM16", Cell Metabolism 6: 38-54, 2007.

International Search Report and the Written Opinion of the International Searching Authority for PCT/US2014/034540, mailed Jul. 22, 2014, 13 pages.

Leung et al., "Regeneration of intervertebral disc by mesenchymal stem cells: potentials, limitations, and future direction", Eur Spine Journal, 2006, vol. 15, (Suppl. 3), pp. S406-S413.

Grayson et al., "Hypoxia enhances proliferation and tissue formation of human mesenchymal stem cells", Biochemical and Biophysical Research Communications, 2007, vol. 358, pp. 948-953.

Grayson et al., "Effects of Hypoxia on Human Mesenchymal Stem Cell Expansion and Plasticity in 3D Constructs", Journal of Cellular Physiology, 2006, vol. 207, pp. 331-339.

Rosova et al., "Hypoxic Preconditioning Results in Increased Motility and Improved Therapeutic Potential of Human Mesenchymal Stem Cells", Stem Cells, 2008, vol. 26, pp. 2173-2182.

\* cited by examiner

BROWN FAT CELL COMPOSITIONS AND METHODS

RELATED APPLICATIONS

This application is a national phase under 35 U.S.C. §371 of International Application No. PCT/US2012/044651 filed on Jun. 28, 2012, which claims priority to and benefit of U.S. Provisional application 61/502,508 filed on Jun. 29, 2011, U.S. Provisional application 61/632,122 filed on Jan. 18, 2012, and U.S. Provisional application 61/632,516 filed on Jan. 25, 2012 the entirety of each of these applications is incorporated by referenced herein.

FIELD OF THE INVENTION

This invention relates to the field of cell culture and more specifically to the culture and use of stem cells.

BACKGROUND

Brown fat is one of two types of adipose tissue found in the human body. During embryogenesis, brown fat is derived from the differentiation of the mesoderm. Brown fat is involved in development and homeostasis by providing metabolic tissue capable of providing heat. Brown fat helps regulate metabolism and nonshivering thermogenesis. In addition, brown fat plays a larger role than white adipose tissue in regulating metabolism. Brown fat makes up 5 percent of the body mass of a human neonate, and less than 1 percent of the body mass of an adult.

Metabolic activity of brown fat decreases with increased body mass index. Similarly, metabolic activity of brown fat decreases with increased body fat percent.

Stem cells have been identified and isolated in various tissues, and white adipose tissue stem cells have been isolated, expanded and shown to have functional therapeutic characteristics. To date, no stem cell population population has been identified in brown adipose tissue.

SUMMARY OF THE INVENTION

Described are methods of developing cell lines, such as stem cell lines, for therapeutic or cosmetic use. For example, the cell lines can be used to treat a wide range of degenerative and metabolic disorders including, but not limited to, obesity, diabetes, hypertension, and cardiac deficiency. Also described are methods of using such cell lines to screen for compounds that play a role in regulating a variety of processes, such as, but not limited to, methylation, homeostasis, and genes involved in the regulation of metabolism, thermogenesis, activation, and/or maintenance of brown and white fat levels in the body.

In one aspect, the invention features a method of generating a stem cell. In one embodiment the steps include obtaining brown fat tissue; isolating a stem cell from the brown fat tissue; and culturing the stem cell in a medium not comprising an animal product, thereby generating a stem cell. In another embodiment the brown fat tissue is from a sample obtained from a subject. In another embodiment the stem cell is positive for one or more of the following cell surface markers: CD63, CD90, HLA ABC, CD 105, CD73, CD166, CD 9, CD44. In another embodiment the stem cell is negative for one or more of the following cell surface markers: CD34, CD19, CD86, HLA DR, Lin, CD106, CD80, CD 117. In still yet another embodiment the stem cell is autogeneic. In another embodiment the stem cell is allogeneic. In another embodiment the medium includes Low Glucose DMEM without phenol red, 0.5-20% Human Platelet Lysate, 1×NEAA, 1× Glutamax, 1× Gentamycin, and 1000 units of Heparin.

In another aspect, the invention features a method of generating a cellular extract of stem cells, progenitor cells or differentiated cells such as activated brown fat adipocytes (e.g., brown fat adipocytes expressing UCP-1 and/or PRDM16) and administrating this extract into fat deposits within the subject, thereby treating obesity.

Another aspect of the invention is a method of treating obesity in a subject. In one embodiment the method includes the steps of removing brown fat from a subject; and administering the brown fat to a fat deposit within the subject, thereby treating obesity in the subject. In one embodiment the fat deposit is a white fat deposit. In another embodiment the fat deposit is a brown fat deposit.

In another aspect, the invention features a method of identifying a compound involved in metabolism regulation, brown fat activation and/or maintenance, comprising contacting an autologous stem cell, progenitor cell or differentiated cell produced by a method described herein with a test compound; determining the level of metabolic activity, thermogenesis, and/or activation of certain genes such as PRDM-16 myf-5 UCP-1, CYC1, NDUFA11, NDUFA13, CMT1A, ELOVL3, DIO2, LHX8, COX8A, CYFIP2, CIDEA, Cox8b, Glut4, of the stem cell, progenitor cell, or differentiated cell in the presence of the test compound; and comparing the level of metabolic activity, thermogenesis and/or gene activity of the stem cell, progenitor cell or differentiated cell in the presence of the test compound to a level of metabolic activity, thermogenesis and/or gene activity of the stem cell, progenitor cell or differentiated cell in the absence of the test compound, wherein a level of metabolic activity, thermogenesis and/or gene activity in the presence of the test compound that is different from a level of metabolic activity, thermogenesis and/or gene activity in the absence of the test compound identifies the test compound as a compound involved in metabolism regulation or brown fat activation, thermogenesis and/or maintenance.

In yet another aspect the invention relates to a method of treating a metabolic disorder in a subject. In one embodiment the method includes the steps of removing a stem cell from a donor; differentiating the stem cell into a brown adipocyte in a medium not comprising an animal product; and administering the brown adipocyte to a fat deposit within the subject, thereby treating the metabolic disorder in the subject. In another embodiment the metabolic disorder is selected from the group consisting of obesity, central obesity, diabetes, hypertension, cardiac deficiency, ischemic cardiac disease, high blood pressure, triglyceride dyslipidemia, HDL dyslipidemia, cholesterol dyslipidemia, elevated fasting plasma glucose, leptin dysregulation, and adipon dysregulation. In still another embodiment the brown adipocyte is administered by subcutaneous injection. In still yet another embodiment the brown adipocyte is administered by systemic injection. In another embodiment the medium contains a differentiation agent selected from the group consisting of insulin, dexamethasone, isobutylmethylxanthine, and indomethacin.

Still yet another aspect of the invention is a method of identifying a compound involved in metabolism regulation. In one embodiment the method includes the steps of isolating a stem cell from the brown fat tissue; culturing the stem cell in a medium not comprising an animal product; contacting the stem cell with a test compound; determining the level of metabolic activity of the stem cell in the presence of the test compound; and comparing the level of metabolic activity of the stem cell in the presence of the test compound to a level of metabolic activity of the stem cell in the absence of the test compound, wherein a level of metabolic activity in the presence of the test compound that is different from a level of metabolic activity in the absence of the test compound identifies the test compound as a compound involved in metabolism regulation. In one embodiment the determining step includes measuring adipogenesis. In another embodiment the method further comprises detecting the levels of one or more of PRDM16, BMP7, UCP1, UCP2, or MYF5. In still yet another embodiment the test compound is selected from the group consisting of protein, antibody, peptide, mutein, polynucleotide, nucleic acid aptamer, and small molecule.

An aspect of the invention relates to differentiating a stem cell into a brown fat cell. In one embodiment the method includes contacting a stem cell with a medium not comprising an animal product, thereby generating a brown fat stem cell. In another embodiment the medium includes an agent selected from the group consisting of: insulin, dexamethasone, isobutylmethylxanthine, indomethacin, T3, rosiglitazone, FNDC5 and combinations thereof. In still yet another embodiment the medium includes insulin, dexamethasone, isobutylmethylxanthine, and indomethacin. In yet another embodiment the brown fat stem cell expresses PRDM-16, PGC-1, or a combination thereof. In still yet another embodiment the brown fat tissue is from a sample obtained from a subject.

BRIEF DESCRIPTION OF DRAWINGS

The present teachings described herein will be more fully understood from the following description of various illustrative embodiments, when read together with the accompanying drawings. It should be understood that the drawings described below are for illustration purposes only and are not intended to limit the scope of the present teachings in any way.

FIGS. 7A and B are micrographs of cells stained with oil red O. FIG. 7A shows large fat droplets (200 μm) and FIG. 7B shows small fat droplets (50 μm).

FIG. 8A shows staining with alizarin red, a marker of osteogenesis.

DETAILED DESCRIPTION

Figure 1:
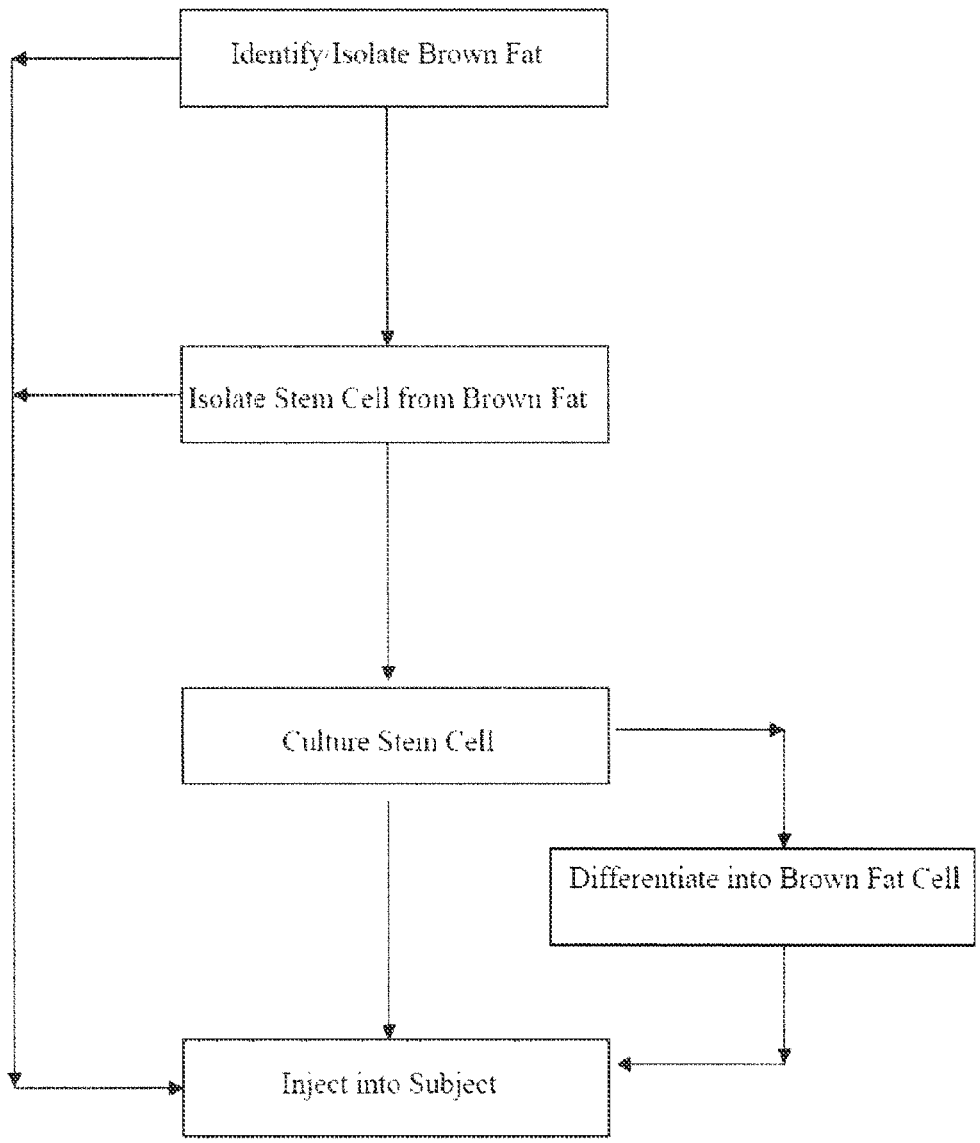
FIG. 1 is a schematic diagram depicting exemplary methods of injecting brown fat cells or brown fat precursor cells into a subject.

The invention is based, at least in part, on the discovery that cells, such as autologous or nonautologous brown fat cells or stem cells, can be isolated and used to modify metabolism and/or thermogenesis in a subject, and/or to treat a wide range of disorders in a subject, such as metabolic disorders. (FIG. 1)

As described herein, brown fat cells and brown fat stem cells can be used therapeutically to treat a number of metabolic disorders. In some embodiments, the metabolic disorder is selected from central obesity (waist circumference of 40 inches or greater in males or 36 inches or greater in females); triglyceride dyslipidemia (1.7 mmol/L (150 mg/dl) or greater); HDL dyslipidemia (less than 40 mg/dl in males, less than 50 mg/dl in females); blood pressure (130/85 mmHg or greater); and elevated fasting plasma glucose (6.1 mmol/L (110 mg/dl) or greater).

The cells isolated can be from, for example, an autologous source or an allogeneic source. However, other sources also can be used.

Cellular products can be made from these cultured stem cells derived from mediastinal fat depots, such as cellular extracts. These cellular extracts then can be used therapeutically.

Cells or stem cells described in this application isolated from brown fat depots also can be used to screen compounds (including naturally occurring compounds) that increase the levels of brown fat, metabolism, and or gene expression profiles that favor higher metabolic activity. Similarly, cells or stem cells described herein can be used to identify compounds (including naturally occurring compounds) that decrease the levels of brown fat, metabolism, and or gene expression profiles that disfavor higher metabolic activity. In some embodiments, the screening is small molecule screening.

As used herein, "treatment" means any manner in which one or more of the symptoms of a disease or disorder are ameliorated or otherwise beneficially altered. As used herein, amelioration of the symptoms of a particular disorder refers to any lessening, whether permanent or temporary, lasting or transient, of the symptoms, which can be attributed to or associated with treatment by the compositions and methods of the present invention.

The terms "effective amount" and "effective to treat," as used herein, refer to an amount or a concentration of one or more of the compositions described herein utilized for a period of time (including acute or chronic administration and periodic or continuous administration) that is effective within the context of its administration for causing an intended effect or physiological outcome.

As used herein, the term "subject" means an animal, human or non-human, to whom treatment according to the methods of the present disclosure is provided. Veterinary and non-veterinary applications are contemplated. The term includes, but is not limited to, mammals. Typical subjects include humans, farm animals, and domestic pets such as cats and dogs. In some embodiments, the subject is a mammal. In some embodiments, the subject is a human subject, e.g., an obese human subject. In some embodiments, the subject is a non-human mammal, e.g., an experimental animal, a companion animal, or an animal that is raised for food.

As used herein, an "isolated" or "purified" cell is a cell substantially free of contaminating components from a cell culture or tissue source from which the cell is derived. "Substantially free" means that a preparation of a selected cell has less than about 50%, (e.g., less than about 40%, 30%, 20%, or 10%) of non-selected components. Such a non-selected component is also referred to herein as "contaminating component." When the isolated cells are recombinantly produced, they can be substantially free of culture medium, i.e., culture medium represents less than about 20%, (e.g., less than about 10% or 5%) of the volume of the cell preparation.

As used herein, "stem cells" are cells capable of both self-renewal and differentiation into many different cell lineages (is pluripotent). "Progenitor cells" refers to a subset of stem cells with phenotypes similar to that of a stem cell. A progenitor cell is capable of self-renewal and is typically multipotent. As used herein, "differentiated cells" refers to a subset of cells with phenotypes of a mature cell type specific to a particular tissue or organ system.

Methods of Obtaining Cells

In general, cells useful in the methods described herein can be obtained from a subject, such as by isolating the cells from a subject, or clinical grade embryonic stem cells can be obtained from a commercial source. In certain embodiments, the cells are part of a tissue sample, such as a brown fat sample, from a subject. The tissue sample can be administered directly into a subject or the cells can be isolated from the tissue and processed as described herein. In other embodiments, the cells are stem cells, such as from a bone marrow biopsy, and can be processed as described herein.

Certain cells that can be used in the methods described herein are unipotent, multipotent, or pluripotent cells and can be of mesodermal origin. In some embodiments, the cells are brown adipose progenitor cells, mature brown fat cells or stem cells. Brown adipose progenitor cells, mature brown fat cells or stem cells can be identified by determining the presence or absence of one or more cell surface expression markers. Exemplary cell surface markers that can be used to identify a brown adipose progenitor cell, mature brown fat cell or stem cell include, but are not limited to, MYF5, UCP-1, PRDM-16, SSEA-4, Sca-1, CD45, Mac-1, CD29 (integrin β1), CD105 (Endoglin), CD166 (ALCAM), desmin, vimentin, and c-kit. In yet other methods, the cells are brown adipose cells.

In any of the methods described herein, the cells can be autologous, syngeneic, allogeneic, or xenogeneic.

Cells suitable for use in the methods described herein can be found in a variety of tissues and organs including, but not limited to, for example, skeletal muscle, cardiac muscle, smooth muscle, prostate, dermis, the cardiovascular system, mammary gland, liver, neonatal skin, calvaria, bone marrow, the intestine, adipose tissue (e.g., white adipose tissue, brown adipose tissue), peripheral blood, mobilized peripheral blood, and umbilical cord. Cells can be isolated from such tissues and organs in a number of known ways, including, e.g., biopsy, apheresis, or liposuction.

In some embodiments, cells are obtained from adipose tissue, e.g., white or brown adipose deposits. For example, brown adipose tissue can be harvested using known means (e.g., by biopsy) from specific anatomical regions of a subject, such as cervical-supraclavicular regions, superior mediastinal regions, and regions superficial or lateral to sternocleidomastoid muscles. Brown adipose tissue can be identified in a number of ways, such as by imaging (e.g., by PET scan). The brown adipose tissue can be subjected to minimal processing (such as by washing with buffer, e.g., DPBS, and mechanically separated into portions) and administered into a subject as described herein.

In other methods, cells, such as brown fat cells, mononuclear cells, progenitor cells, or stem cells, can be isolated from contaminating components of the tissue sample. For example, the tissue sample can be treated with an enzyme such as collagenase (e.g., Type I, II, or III), dispase, hyaluronidase, or elastase and cells can be isolated by filtration or centrifugation. Alternatively, the tissue sample can be treated chemically, such as with EDTA, and cells can be isolated using, e.g., mechanical disruption (e.g., vortexing). The isolated cells can be washed with a suitable buffer, such as DPBS.

In some methods, cells are isolated from a bone marrow sample of a subject. For example, a bone marrow sample can be obtained using needle aspiration or other known technique. In certain instances, cells can be isolated from a bone marrow sample using a Ficoll-Hypaq density gradient.

In yet other methods, cells are isolated from skin of a subject. For example, a punch biopsy can be used to obtain a skin sample. In one exemplary method, a punch biopsy is used to obtain a 0.5 cm piece of skin, which is washed three times with DPBS, and the dermis is removed from the biopsy. The skin is then cut into small (about 3 mm) sections and plated onto the wells of a 6-well tissue culture plate with a sterile cover slip over the tissue and the cells cultured.

Methods of Culturing Cells

In certain methods, cells obtained as described herein are maintained in a suitable culture medium, e.g., a culture medium not comprising an animal-based product (such as bovine serum or calf serum) in order to obtain a larger population of cells. The culture methods can include allowing the cells to undergo sufficient rounds of doubling, e.g., to produce either a clonal cell strain or a heterogeneous cell strain of desired size, e.g., a sufficient number to provide a therapeutic effect to a subject, or a sufficient number to establish a stable cell line. For example, cells can be cultured at 37° C. for a period of 3-6 weeks after an initial biopsy.

The culture media used in the methods described herein do not include animal-based products. An exemplary culture medium suitable for the methods described herein can include human platelet lysate and an anticoagulant, such as heparin or acid-citrate-dextrose. Another exemplary culture medium includes human pooled AB type serum and an anticoagulant. Other examples of culture medium can include Modified Eagle Medium (MEM) (such as Dulbecco's MEM or alpha MEM) supplemented with glycine, L-alanine, L-asparagine, L-aspartic acid, L-glutamic acid, L-proline, L-serine, L-glutamine, and an antibiotic. One exemplary culture medium includes: DMEM (low glucose, without phenol red); 0.5-20% human platelet lysate; 1× non-essential amino acids (NEAA); 1× Glutamax; 1× gentamycin, and 1000 units of heparin.

In some embodiments, the cells can be maintained in the culture medium under standard conditions, such as described in, e.g., Freshney (1994) Culture of Animal Cells, a Manual of Basic Technique, third edition, Wiley-Liss, New York.

In certain embodiments, the cells are cultured in human platelet lysate or human pooled AB type serum derived from subjects who have been exposed to cold temperatures, e.g., a temperature suitable to generate a sympathetic nervous system response in the subject.

In other embodiments, the cells can be maintained in a hypoxic environment (e.g., 0 to about 5% $O_2$ at 37° C.).

In certain embodiments, cultured cells can express MYF-5, BMP7, and/or PRDM16, SSEA4. In other embodiments, cells cultured from muscle tissue can express SCA1 and not express c-Kit or CD45.

Methods of Differentiating Cells

In certain embodiments, cells obtained as described herein are maintained in a suitable differentiation medium, e.g., a medium not comprising an animal-based product. For example, stem cells can be maintained in a differentiation medium for a time sufficient to result in the differentiation of the stem cells into brown adipocyte progenitor cells or brown adipocytes. In particular embodiments, cells are maintained in a differentiation medium for a time sufficient to result in the differentiation of the stem cells into MYF5 expressing cells. In certain instances, cells are maintained in the differentiation medium for, e.g., 1-5 days, 5-10 days, 10-14 days, 14-21 days, 21-28 days, or longer.

In some embodiments, the differentiation medium includes one or more chemical or hormone differentiation inducers and/or thiazolidinediones (as described in, e.g., Klien et al., J. Biol. Chem. 274:34795-34802 (1999); Hauner et al., J. Clin. Invest. 84:1663-1670 (1989)). In some instances, the differentiation medium includes insulin, dexamethasone, isobutylmethylxanthine, and indomethacin and rosiglitazone. One exemplary differentiation medium includes DMEM (low glucose without phenol red); 0.5%-20% Human Platelet Lysate; 1×NEAA; 1× Glutamax; 1× gentamycin; 1000 units of heparin; 10 ug/mL of insulin; 1 uM dexamethasone; 200 uM indomethacin; and 0.5 mM isobutylmethylxanthine. In another embodiment, the differentiation medium includes BMP7. In another embodiment, the differentiation medium includes DMEM (low glucose without phenol red); 0.5%-20% Human Platelet Lysate; 1×NEAA; 1× Glutamax; 1× gentamycin; 1000 units of heparin; 0.5 mM isobutylmethylxanthine, 125 nM indomethacin, 5 uM dexamethosaone, 850 nM insulin, 1 nM T3, and 1 uM rosiglitazone. In another embodiment, the differentiation medium includes DMEM (low glucose without phenol red); 0.5%-20% Human Platelet Lysate; 1×NEAA; 1× Glutamax; 1× gentamycin; 1000 units of heparin; 0.5 mM isobutylmethylxanthine, 125 nM indomethacin, 5 uM dexamethosaone, 850 nM insulin, 1 nM T3, and 1 uM rosiglitazone and 20 nM FNDC5.

In some instances, the cells are maintained in differentiation medium until one or more markers of brown adipocyte differentiation are detected. Non-limiting examples of markers of differentiation include the expression of cell death-inducing DFF45-like effector A (CIDEA), Type II deiodinaie, PPAR gamma coactivator (PGC)-1 alpha, PGC-1 beta, uncoupling protein (e.g., UCP1), PRDM16, or CIG30, PRDM-16, CYC1, NDUFA11, NDUFA13, CMT1A, ELOVL3, DIO2, LHX8, COX8A, CYFIP2, Cox8b, Glut4.

In some embodiments, the methods include exposing the cells to cold shock by culturing or differentiating the cells during daily cycles of 4° C.-25 C for one hour followed by culture at standard conditions (37° C., 5% $CO_2$ or hypoxic conditions).

In some embodiments, the methods include evaluating the level of adipogenesis following maintenance in a differentiation medium. Adipogenesis can be evaluated by measuring, e.g., lipid accumulation (e.g., using oil red-o (ORO) staining), cell morphology (e.g., using visual, e.g., microscopic, inspection of the cells), or cell thermodynamics (e.g., cytochrome oxidase activity, Na+-K+-ATPase enzyme units, or other enzymes involved in brown adipocyte thermogenesis). In addition, in some embodiments, functional brown fat adipogenesis following differentiation can be determined by fatty acid uptake assays or oxygen consumption rate.

Further Processing Methods

In some embodiments, cells obtained as described herein can be subjected to additional processing before administration into a subject. In certain embodiments, a cell obtained as described herein can be recombinantly modified to express one or more genes, e.g., a gene involved in brown adipogenesis. For example, a cell can be transfected with one or more nucleic acids encoding DFF45-like effector A (CIDEA), Type II deiodinaie, PPAR gamma coactivator (PGC)-1 alpha, PGC-1 beta, uncoupling protein (e.g., UCP1), PRDM16, or CIG30, PRDM-16, CYC1, NDUFA11, NDUFA13, CMT1A, ELOVL3, DIO2, LHX8, COX8A, CYFIP2, Cox8b, Glut4 or combinations of the genes, prior to administration into a subject.

In other embodiments, the cells can be pluripotent stem cells artificially derived (e.g., differentiated or partially differentiated) from a non-pluripotent cell. For example, skin cells, such as dermal fibroblasts, can be reprogrammed to a pluripotent state by transfection with OCT4, Nanog, or SSEA4. Such cells are known in the art as induced pluripotent stem cells. In other embodiments the cells can be further manipulated after becoming pluripotent by transfection with one or more nucleic acids encoding DFF45-like effector A (CIDEA), Type II deiodinaie, PPAR gamma coactivator (PGC)-1 alpha, PGC-1 beta, uncoupling protein (e.g., UCP1), PRDM16, or CIG30, PRDM-16, CYC1, NDUFA11, NDUFA13, CMT1A, ELOVL3, DIO2, LHX8, COX8A, CYFIP2, Cox8b, Glut4 or combinations of the genes, (ie. PPARG2, CEBPB, PRDM16)

In further embodiments, a cell can be mitotically inactivated prior to administration into a subject. Without wishing to be bound by theory, it is believed that upon administration to a subject, cells obtained and/or treated as described herein express certain factors that may have a paracrine effect on surrounding cells and tissues. Accordingly, mitotic inactivation prevents further cell division while allowing the inactivated cells to maintain the paracrine effect. In certain embodiments, cells can be treated with chemical or gamma irradiation sufficient to mitotically inactivate the cells.

In some embodiments, a cell extract or lysate can be prepared from a cell described herein and administered to a subject. For example, cells can be obtained and cultured, and about $10^6$ to about $10^{10}$ cells can be collected and used to prepare a cell-free extract using known methods. In one exemplary method, an extract is prepared by subjecting the collected cells to freeze-thaw cycles (e.g., 1, 2, 3, 4, 5, or more freeze-thaw cycles) using an ethanol/dry ice bath. The extract is then centrifuged (e.g., at about 14,000 rpm) to remove insoluble material. The extract can then be administered to a subject.

Expression Methods

In certain embodiments, a cell described herein can be recombinantly modified to express one or more genes. Such nucleic acids can be incorporated into an expression vector. Expression vectors comprising a nucleic acid sequence described herein can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, poxvirus, alphavirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramicidin S, artificial viral envelopes or other such intracellular carriers, as well as direct injection of the gene construct or $CaPO_4$ precipitation carried out in vivo.

In some embodiments, the expression vector is a viral vector containing one or more nucleic acid sequences (e.g., cDNA). Retrovirus vectors can be used as a recombinant gene delivery system for the transfer of exogenous genes in vivo, particularly into humans as is known to one skilled in the art. (Protocols for producing recombinant retroviruses and for infecting cells in vitro or in vivo with such viruses can be found in Ausubel, et al., eds., *Current Protocols in Molecular Biology*, Greene Publishing Associates (1989), Sections 9.10-9.14, and other standard laboratory manuals. Another viral gene delivery system useful in the present methods utilizes adenovirus-derived. Yet another viral vector system useful for delivery of nucleic acids is the adeno-associated virus (AAV) as is known to one skilled in the art.

In addition to viral transfer methods, such as those illustrated above, non-viral methods can also be employed to express a nucleic acid into a cell described herein. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-cationic conjugates such as polyamine and polylysine, and artificial viral envelopes. Other embodiments include plasmid injection systems as known to one skilled in the art. Other non-viral vectors include a scaffold/matrix attached region (S/MAR)-based vector. In particular embodiments, a cell described herein is transfected with an S/MAR-PRDM 16 construct, an S/MAR-BMP-7/PRDM16 construct, or an S/MAR-BMP-7 construct. In another embodiment the cell is transfected with an S/MAR construct containing one or more nucleic acids encoding DFF45-like effector A (CIDEA), Type II deiodinaie, PPAR gamma coactivator (PGC)-1 alpha, PGC-1 beta, uncoupling protein (e.g., UCP1), PRDM16, or CIG30, PRDM-16, CYC1, NDUFA11, NDUFA13, CMT1A, ELOVL3, DIO2, LHX8, COX8A, CYFIP2, Cox8b, Glut4 or combinations of the genes or a combination of them (i.e. PPARG2, CEBPB, PRDM16).

In some embodiments, a nucleic acid can be expressed using naked DNA constructs and/or DNA vector based constructs as is known to one skilled in the art. In some embodiments, DNA vectors can be introduced into target cells via conventional transformation or transfection techniques. As used herein, the terms "transformation" and "transfection" are intended to refer to a variety of art-recognized techniques for introducing foreign nucleic acid (e.g., DNA) into a target cell, including calcium phosphate or calcium chloride co-precipitation, DEAE-dextran-mediated transfection, lipofection, electroporation, gene gun, sonoporation, or magnetofection.

All the molecular biological techniques required to generate an expression construct described herein are standard techniques that will be appreciated by one of skill in the art.

Methods of Administration

Methods described herein can include implanting tissue or cells, e.g., cells obtained or isolated as described herein, into a subject to be treated. The cells can be differentiated brown adipocytes (e.g., isolated brown adipocytes or differentiated adipocytes produced as described herein), or can be stem cells or undifferentiated cells, which cells, or their progeny (i.e., daughter cells), will differentiate into brown adipocytes after implantation. These methods are useful, e.g., for modifying metabolism in a subject as described herein.

Prior to administration into a subject, the cells can be washed (e.g., in isotonic PBS) to remove any contaminants, including contaminating components of tissue sample, culture media or differentiation media, before implantation. The number of required cells is variable and depends on a variety of factors, including but not limited to, the cell type used, the site of implantation of the cells (for example, the number of cells that can be used can be limited by the anatomical site of implantation), and the age, surface area, and clinical condition of the subject. In some embodiments, at least about $10^5$, $10^6$, $10^7$, $10^8$, $10^9$, or about $10^{10}$ cells are implanted into the subject.

Methods for implanting cells within a subject are known in the art, e.g., using a delivery system configured to allow the introduction of cells into a subject. In general, the delivery system can include a reservoir containing cells and a needle in fluid communication with the reservoir. Such delivery systems are also within the scope of the invention. Generally, such delivery systems are maintained in a sterile manner. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used.

The cells can be in a pharmaceutically acceptable carrier, with or without a scaffold, matrix, or other implantable device to which the cells can attach (examples include carriers made of, e.g., collagen, fibronectin, elastin, cellulose acetate, cellulose nitrate, polysaccharide, fibrin, gelatin, and combinations thereof). Initially 1,000,000 cells where seeded onto porous extracellular scaffolds and cultured for 5 days. Differentiation into brown adipose was initiated by adding DMEM (low glucose without phenol red) containing 10% Human Platelet Lysate;
1×NEAA; 1× Glutamax;
1× gentamycin;
1000 units of heparin;
0.5 mM isobutylmethylxanthine,
125 nM indomethacin,
5 uM dexamethosaone,
850 nM insulin,
1 nM T3,
1 uM rosiglitazone.

and the cells were grown in this medium for 2 days followed by further differentiation for an additional 18 days in media composed of:

DMEM (low glucose without phenol red);
10% Human Platelet Lysate;
1×NEAA; 1× Glutamax;
1× gentamycin;
1000 units of heparin; 0.5 mM isobutylmethylxanthine,
125 nM indomethacin,
5 uM dexamethosaone,
850 nM insulin,
1 nM T3,
1 uM rosiglitazone
20 nM FNDC5.

Cells implanted using scaffolding were shown under scanning electron microscopy to attach to the scaffold. Further measurements of fatty acid uptake by the cells showed that the cells were metabolically active.

In particular instances, the cells are implanted into white fat or brown fat in the subject, and/or into or near an anatomical region containing white fat or brown fat.

Where non-immunologically compatible cells are used (e.g., where non-autologous cells are administered to a subject), an immunosuppressive compound, e.g., a drug or antibody, can be administered to the subject at a dosage sufficient to achieve inhibition of rejection of the cells. Dosage ranges for immunosuppressive drugs are known in the art. Dosage values may vary according to factors such as the disease state, age, sex, and weight of the individual.

Subjects

The methods and compositions described herein are useful for the treatment of metabolic disorders. Generally, the methods include administering an effective amount of cells described herein to a subject in need thereof, including a subject that has been diagnosed to be in need of such treatment. Subjects can include mammals In some embodiments, the methods include identifying a subject in need of treatment (e.g., a subject having or at risk of developing a metabolic disorder), and administering to the subject an effective amount of tissue or cells described herein. In certain instances, the subject is diagnosed as being an overweight or obese subject, e.g., with a body mass index (BMI) of 25-29 or 30 or above or a subject with a weight related disorder. A subject in need of treatment with the methods described herein can be selected based on the subject's body weight or body mass index. In some embodiments, the methods include evaluating the subject for one or more of: weight, adipose tissue stores, adipose tissue morphology, insulin levels, insulin metabolism, glucose levels, thermogenic capacity, and cold sensitivity. In some embodiments, subject selection can include assessing the amount or activity of brown adipose tissue in the subject and recording these observations.

The evaluation can be performed before, during, and/or after the administration of the cells described herein. For example, the evaluation can be performed at least 1 day, 2 days, 4, 7, 14, 21, 30 or more days before and/or after the administration of cells described herein.

Metabolism and Metabolic Disorders

Metabolism is a cascade of chemical reactions that regulate the mechanisms by which living organisms regulate, maintain and respond to intrinsic and extrinsic factors that affect their ability to maintain, grow, and reproduce. An imbalance of this metabolic activity can lead to downstream cellular events that can give rise to a number of degenerative disorders. Such disorders can bring about not only symptoms of a wide range of diseases, but can interfere with proper methylation of the imprinting pattern of male and female germ cells, thus establishing a genetic predisposition in the new generation to degenerative disorders.

In certain embodiments, the tissue or cells described herein are administered to a subject to modify, e.g., increase, metabolic activity in the subject. In certain embodiments, the subject has a disorder such as, but not limited to, obesity, osteoarthritis, hypertension, diabetes, an auto-immune disorder, stroke, kidney failure, neoplasia, or a cardiac deficiency such as ischemic heart disease. In particular instances, the administration of cells described herein treat the disorder.

In other embodiments, subjects can be screened for levels of adipogenesis markers, such as DFF45-like effector A (CIDEA), Type II deiodinaie, PPAR gamma coactivator (PGC)-1 alpha, PGC-1 beta, uncoupling protein (e.g., UCP1), PRDM16, or CIG30, PRDM-16, CYC1, NDUFA11, NDUFA13, CMT1A, ELOVL3, DIO2, LHX8, COX8A, CYFIP2, Cox8b, Glut4, and/or BMP7, and the information used as a diagnostic tool for obesity, hypertension, diabetes or ischemic cardiac disease. For example, an adipose tissue sample or a blood sample can be obtained from a subject and the level of DFF45-like effector A (CIDEA), Type II deiodinaie, PPAR gamma coactivator (PGC)-1 alpha, PGC-1 beta, uncoupling protein (e.g., UCP1), PRDM16, or CIG30, PRDM-16, CYC1, NDUFA11, NDUFA13, CMT1A, ELOVL3, DIO2, LHX8, COX8A, CYFIP2, Cox8b, Glut4, and/or BMP7 can be measured in the sample. A level of DFF45-like effector A (CIDEA), Type II deiodinaie, PPAR gamma coactivator (PGC)-1 alpha, PGC-1 beta, uncoupling protein (e.g., UCP1), PRDM16, or CIG30, PRDM-16, CYC1, NDUFA11, NDUFA13, CMT1A, ELOVL3, DIO2, LHX8, COX8A, CYFIP2, Cox8b, Glut4, and/or BMP7 below a predetermined level indicates the subject has, or is at risk of developing, a metabolic disorder, such as obesity, hypertension, diabetes or ischemic cardiac disease. The predetermined level can be the level of a marker in a corresponding sample from a subject not having the metabolic disorder. In yet other embodiments, the levels of brown fat and white fat in a subject can be measured, e.g., using PET scan, and a ratio of brown fat to white fat can be determined. A ratio of brown fat to white fat less than a predetermined level can indicate the subject has, or is at risk of developing, a metabolic disorder, such as obesity, hypertension, diabetes or ischemic cardiac disease.

Methods of Screening for Adipogenesis Compounds

Cells isolated or cultured as described herein can be used to screen for compounds that modify, e.g., increase or reduce, metabolic activity. In some embodiments, a cell, e.g., a brown adipocyte progenitor cell, differentiated cell or stem cell, can be contacted with a test compound and the level of a marker for adipogenesis, e.g., a marker described herein (e.g., PRDM16, BMP7, UCP1 or MYF5) can be measured. A test compound that increases the level of a marker for adipogenesis relative to a cell not contacted with the test compound is identified as a compound that increases metabolic activity, whereas a test compound that reduces a marker for adipogenesis is identified as a compound that decreases metabolic activity. In another embodiment the cell is a white adipocyte and it is transfected with a construct expressing a reporter gene (i.e. GFP, luciferase) under the control of DFF45-like effector A (CIDEA), Type II deiodinaie, PPAR gamma coactivator (PGC)-1 alpha, PGC-1 beta, uncoupling protein (e.g., UCP1), PRDM16, or CIG30, PRDM-16, CYC1, NDUFA11, NDUFA13, CMT1A, ELOVL3, DIO2, LHX8, COX8A, CYFIP2, Cox8b, Glut4 or a combination of them. A test compound that increases the level of a marker for adipogenesis relative to a cell not contacted with the test compound is identified as a compound that increases metabolic activity, whereas a test compound that reduces a marker for adipogenesis is identified as a compound that decreases metabolic activity In one exemplary method, a cell described herein is transfected with an expression vector that includes a nucleic acid encoding DFF45-like effector A (CIDEA), Type II deiodinaie, PPAR gamma coactivator (PGC)-1 alpha, PGC-1 beta, uncoupling protein (e.g., UCP1), PRDM16, or CIG30, PRDM-16, CYC1, NDUFA11, NDUFA13, CMT1A, ELOVL3, DIO2, LHX8, COX8A, CYFIP2, Cox8b, Glut4, BMP7, MYF5 or a combination of them, under the control of an inducible promoter. Nonlimiting examples of such promoters include chemically-regulated promoters (i.e tetracycline, steroids and metals), or temperature specific promoters that will activate and promote expression at a permissive temperature, such as below normal body temperature of a subject.

In one example, a temperature specific promoter is placed in a viral or non viral vector upstream of a nucleic acid encoding DFF45-like effector A (CIDEA), Type II deiodinaie, PPAR gamma coactivator (PGC)-1 alpha, PGC-1 beta, uncoupling protein (e.g., UCP1), PRDM16, or CIG30, PRDM-16, CYC1, NDUFA11, NDUFA13, CMT1A, ELOVL3, DIO2, LHX8, COX8A, CYFIP2, Cox8b, Glut4 or a combination of them, MYF5 and/or BMP7. A cell isolated from adipose tissue (white or brown), bone marrow, skin, muscle, or umbilical cord is transfected with the vector. The cell is then cultured under the permissive temperature (which allows gene expression from the promoter) in the presence or absence of a test compound, and the effect of the test compound on adipogenesis is determined.

Test compounds include, e.g., proteins (including antibodies), muteins, polynucleotides, nucleic acid aptamers, hormones (i.e Irisin) and peptide and nonpeptide small organic molecules. Test compounds can be isolated from natural sources, prepared synthetically or recombinantly, or any combination of the same. Particular, nonlimiting examples of test compounds include 2,4-dinitrophenol, Ephedrine, Sibutramine, FGF21, Bile acids, and Beta-3 adrenergic receptor agonists.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following examples. The examples are provided for illustrative purposes only. They are not to be construed as limiting the scope or content of the disclosure in any way.

EXAMPLES

Example 1

Brown Fat Isolation Processing

In one example, a patient first underwent a $^{18}$F-fluorodeoxyglucose ($^{18}$F-FDG) PET-CT scan to identify brown fat deposits. Prior to undergoing the PET-CT scan, the patient was exposed to temperatures ranging from 1° C.-25° C. (to increase the uptake of $^{18}$F-FDG) for 1-2 hours per day for a period of one month. Deposits identified within the cervical-supraclavicular and mediastinal area were biopsied using a needle. Brown fat biopsies were washed three times in DPBS (−) and either treated with 0.075%-0.2% Collagenase Type 1A with vigorous shaking at 37° C. for 30-60 minutes or treated with EDTA for 30 minutes and subjected mechanical tissue disruption for 5-30 minutes. The tissue/cells were washed three times with DABS (−), and $1\times10^6$-$1\times10^{10}$ cells were injected into white fat deposits in the patient. Optionally, following enzymatic or mechanical tissue/cell isolation, the tissue/cells were exposed to cold temperature (0° C.-4° C.) for 1-48 hours prior to injection.

Example 2

Brown Fat Culture

In this example, cells were cultured prior to injection into a patient. The cells obtained from Example 1 were plated into hyper flasks at a concentration of 1000 cells/cm$^2$ in a culture medium comprising in this embodiment:
 DMEM Low Glucose without phenol red
 0.5-20% Human Platelet Lysate
 1×NEAA
 1× Glutamax
 1× Gentamycin
 1000 units of Heparin
The cells were cultured for 3-6 weeks. The cells were then characterized by flow-cytometry and analyzed for the expression of one or more of the following markers: SCA-1, CD34, SSEA1, SSEA4, OCT4, CD31, Wnt5a, Telomerase activity, alpha-SMA, STRO-1, MYF5, PRDM16, or UCP1. The cells were then expanded to concentrations of $1\times10^6$-$1\times10^{10}$ for implantation into white fat deposits of the patient.

Example 3

Differentiation of Cells into Brown Fat Cells

In this example, cells (such as stem cells or precursor brown adipocytes) obtained from a brown fat deposit of a patient were differentiated and subsequently injected into a patient. The cells obtained from Example 1 were plated out at 1000 cells/cm$^2$ in hyper flasks containing a differentiation medium comprising, in this embodiment:
 DMEM Low Glucose with out phenol red
 0.5-20% Human Platelet Lysate
 1×NEAA
 1× Glutamax
 1× Gentamycin
 1000 units of Heparin
 10 ug/mL of insulin
 1 uM Dexamethasone
 200 uM Indomethacin
 0.5 mM Isobutylmethylxanthine
 In an alternative embodiment the differentiation medium included:
 DMEM (low glucose without phenol red)
 0.5%-20% Human Platelet Lysate;
 1×NEAA; 1× Glutamax;
 1× gentamycin;
 1000 units of heparin;
 0.5 mM isobutylmethylxanthine,
 125 nM indomethacin,
 5 uM dexamethosaone,
 850 nM insulin,
 1 nM T3,
 1 uM rosiglitazone.
and the cells were grown in this medium for 2-6 days followed by further differentiation for an additional 6-21 days in media composed of:
 DMEM (low glucose without phenol red);
 0.5%-20% Human Platelet Lysate;
 1×NEAR; 1× Glutamax;
 1× gentamycin;
 1000 units of heparin; 0.5 mM isobutylmethylxanthine,
 125 nM indomethacin,
 5 uM dexamethosaone,
 850 nM insulin,
 1 nM T3,
 1 uM rosiglitazone
 20 nM FNDC5.
After being maintained in the differentiation medium for 10-30 days, cells were characterized by expression of DFF45-like effector A (CIDEA), Type II deiodinaie, PPAR gamma coactivator (PGC)-1 alpha, PGC-1 beta, uncoupling protein (e.g., UCP1), PRDM16, or CIG30, PRDM-16, CYC1, NDUFA11, NDUFA13, CMT1A, ELOVL3, DIO2, LHX8, COX8A, CYFIP2, Cox8b, Glut4. $1\times10^6$-$1\times10^{10}$ of the cells are then prepared for injection into the patient.

Example 4

Culturing and Differentiating Embryonic Stem Cells

In this example clinical grade embryonic stem cells were first grown and expanded. The cells were then differentiated into brown fat pre-adipocytes or fully differentiated brown fat adipocytes by exposing the cells, in one embodiment, to the following media:
DMEM Low Glucose with out phenol red
0.5-20% Human Platelet Lysate
1×NEAA
1× Glutamax
1× Gentamycin
1000 units of Heparin
10 ug/mL of insulin
1 uM Dexamethasone
200 uM Indomethacin
0.5 mM Isobutylmethylxanthine In another embodiment, the cells were grown for 2-6 days in a medium comprising:
DMEM (low glucose without phenol red);
0.5%-20% Human Platelet Lysate;
1×NEAA;
1× Glutamax;
1× gentamycin;
1000 units of heparin;
0.5 mM isobutylmethylxanthine,
125 nM indomethacin,
5 uM dexamethosaone,
850 nM insulin,
1 nM T3,
1 uM rosiglitazone.

This is followed by further differentiation for an additional 6-21 days in media composed of
DMEM (low glucose without phenol red);
0.5%-20% Human Platelet Lysate;
1×NEAA;
1× Glutamax;
1× gentamycin;
1000 units of heparin;
0.5 mM isobutylmethylxanthine,
125 nM indomethacin,
5 uM dexamethosaone, 850 nM insulin,
1 nM T3,
1 uM rosiglitazone,
20 nM FNDC5.

Optionally, the cells were transfected, prior to differentiation or after differentiation, with a non-viral vector (scaffold/matrix attached region (S/MAR)) with a PRDM-16 gene by itself or in tandem with BMP-7 or MYF-5 or DFF45-like effector A (CIDEA), Type II deiodinaie, PPAR gamma coactivator (PGC)-1 alpha, PGC-1 beta, uncoupling protein (e.g., UCP1), PRDM16, or CIG30, PRDM-16, CYC1, NDUFA11, NDUFA13, CMT1A, ELOVL3, DIO2, LHX8, COX8A, CYFIP2, Cox8b, Glut4 or a combination of them driven by a strong promoter such as CAGGS or PGK. The cells were then inactivated with a chemical based method such as mitomycin C or gamma irradiation and implanted into a patient at concentrations of $1\times10^6$-$1\times10^{10}$ cells.

Example 5

Brown Fat Human Depot Biopsy

In this example a patient underwent $^{18}$F-PET-CT scan to identify tissue that has metabolic activity. An area with high metabolic activity was identified within the human mediastinum region of the patient. In addition, this patient was to undergo routine cardiothoracic surgery. At the time of surgery the region was exposed, and within this region 5×5 cm brown fat depot was dissected out and placed into sterile saline.

A brown fat depot was discovered in the mediastinum that contains a population of stem cells that express unique markers different than those found in other stem cells, including stem cells isolated from white adipose depots. These newly identified stem cells were separated from the mediastinum brown fat depot and cultured for greater than 20 passages and still retained a normal karyotype. These cells also are capable of undergoing adipogenesis (white and brown), osteogenesis, and chondrogenesis.

Example 6

Isolation of Cells from Human Brown Fat Depot Biopsy

The brown fat human depot isolated in Example 5 was washed 5-10 times in sterile saline. The biopsy was cut using scissors until pieces are approximately 0.1-0.5 cm in size. The material was washed 3 times by centrifuging at 1200 RPM for 5 minutes. The material was then digested using either collagenase or dispase for no longer than an hour in a shaking water bath set at 37 C. After digestion was complete the enzymatic reaction was terminated by adding equal volume of complete media. The material was then filtered using a 100 uM filter and the single cell suspension was washed 3 times with complete medium.

Example 7

Culture of Cells Isolated from Brown Fat Human Depot Biopsy

Figure 2:
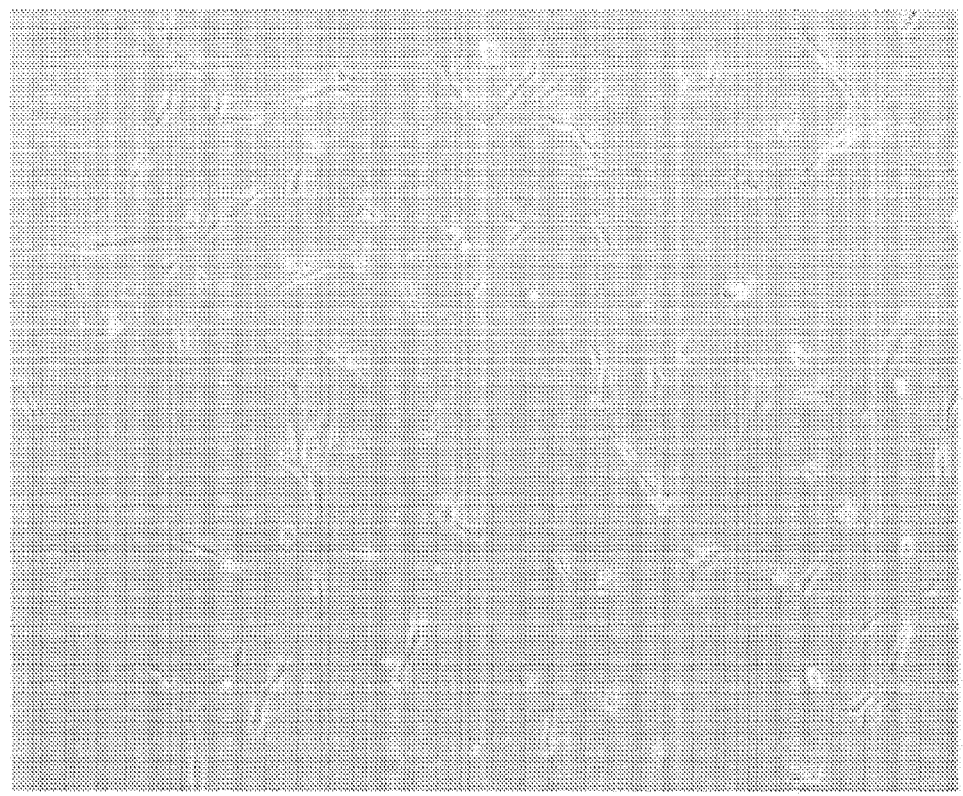
FIG. 2 is a micrograph of a cell culture ready for passaging.
Figure 3:
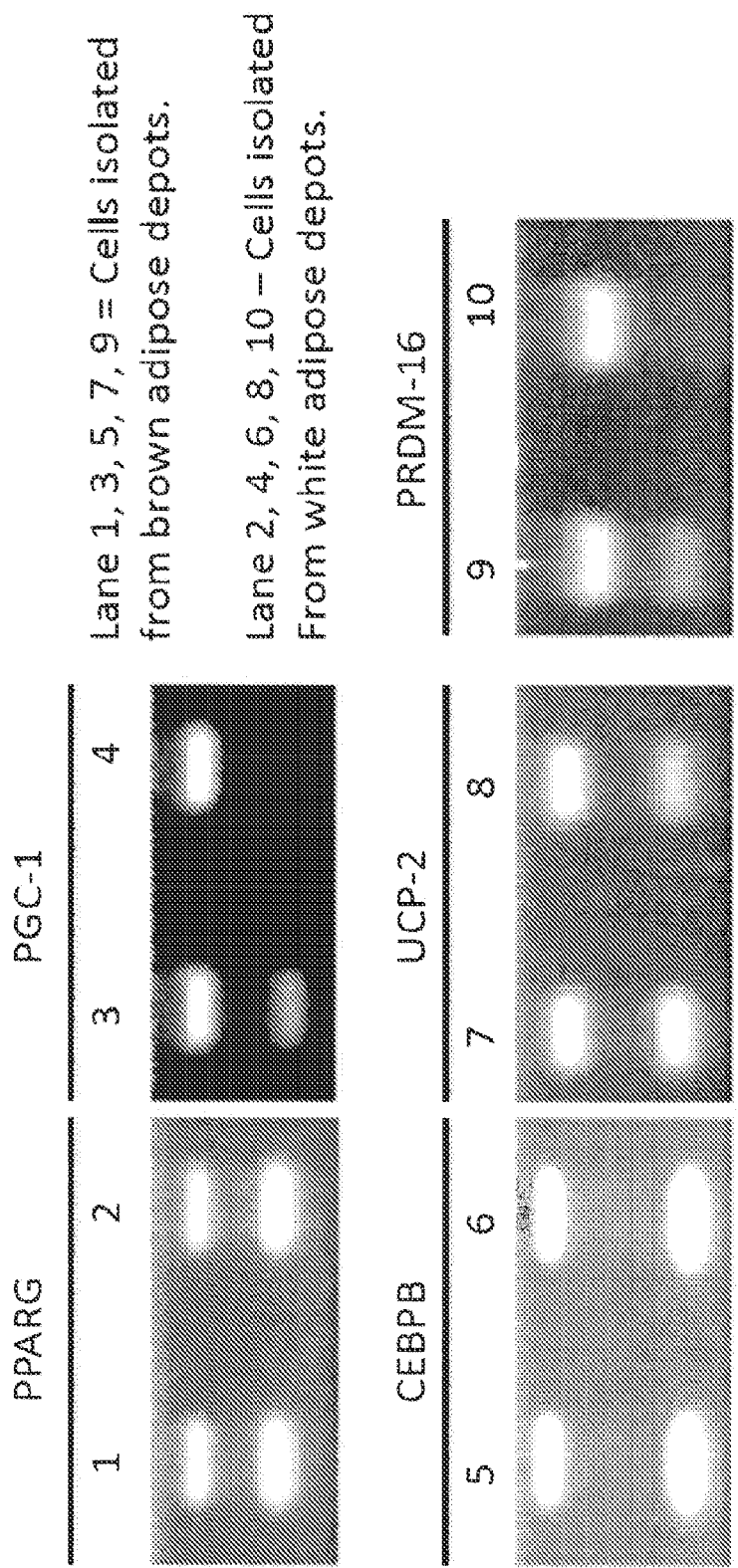
FIG. 3 are images showing gene expression by RT-PCR in white adipose depots and brown adipose depots.

The single cell suspension described in Example 6 was plated onto cell culture flasks at a concentration of 5,000-10,000 cells/cm2. After approximately 3-6 days the cells were ready for passaging (FIG. 2). The cells after undergoing more than 10 passages showed a normal karyotype. RT-PCR analysis of the cultured brown fat cells demonstrated that they were positive for CEBPB, UCP-1, UCP-2, PPARG, PGC-1, PRDM-16. It is important to note that cells isolated from white adipose depots were negative for PRDM-16, and PGC-1. (FIG. 3). Accordingly, PRDM-16 and/or PGC-1 expression can be used to differentiate between white adipose cells and brown adipose cells. Moreover, CEBPB, UCP-1, UCP-2, PPARG, PGC-1, PRDM-16 can be used as markers to identify brown adipose cells.

Figure 4:
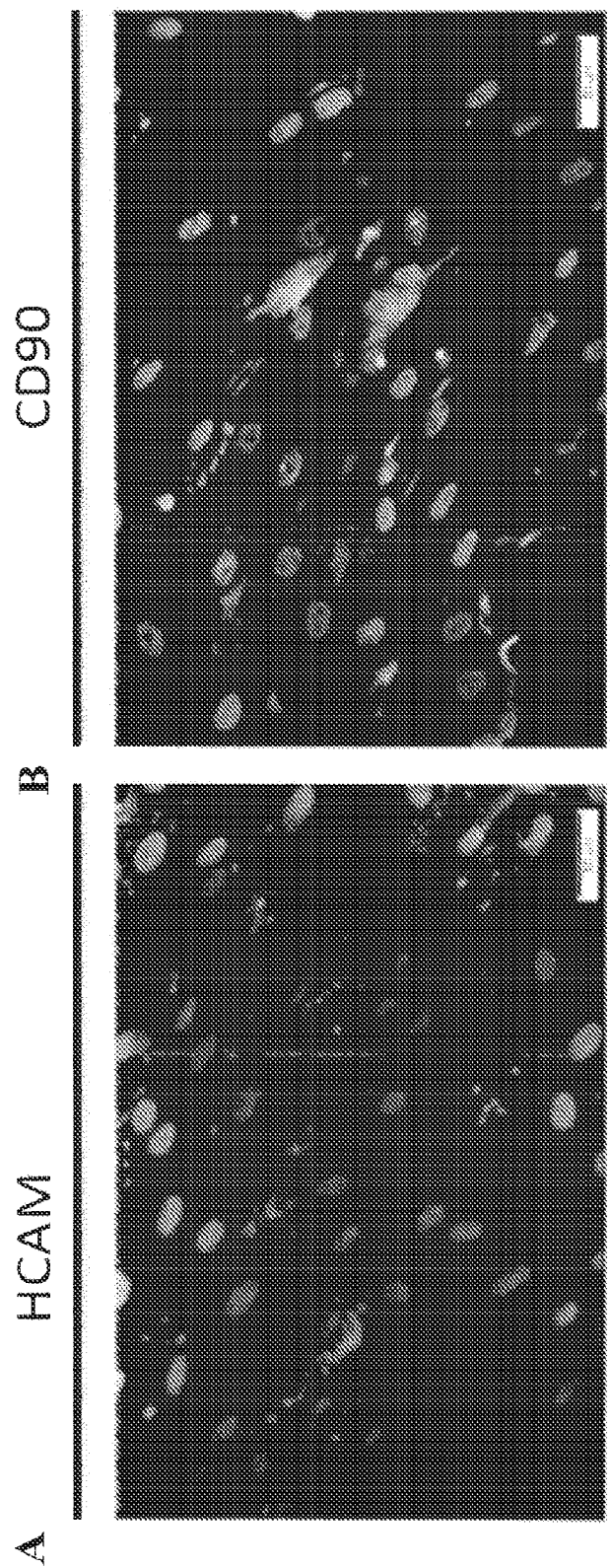
FIGS. 4 A and B are fluorescent micrographs of cells stained with stem cell markers.
Figure 5A:
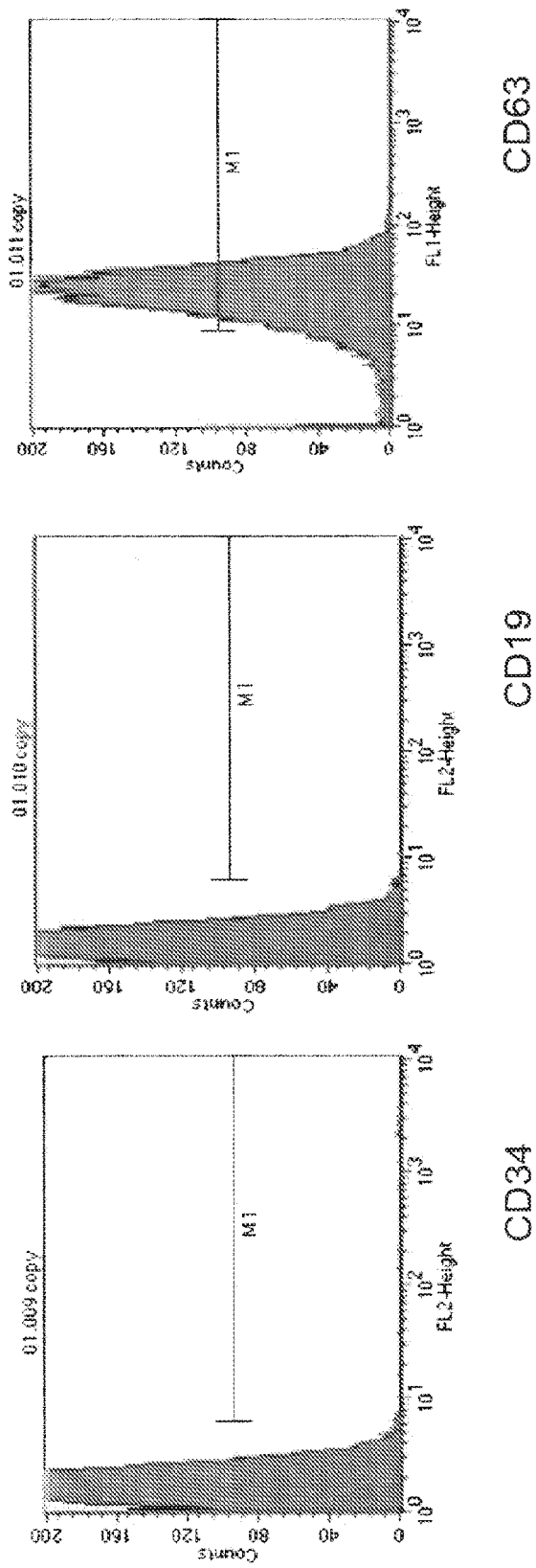
FIGS. 5A-F is a series of graphs showing detection by flow cytometry of various cell type markers.
Figure 5B:
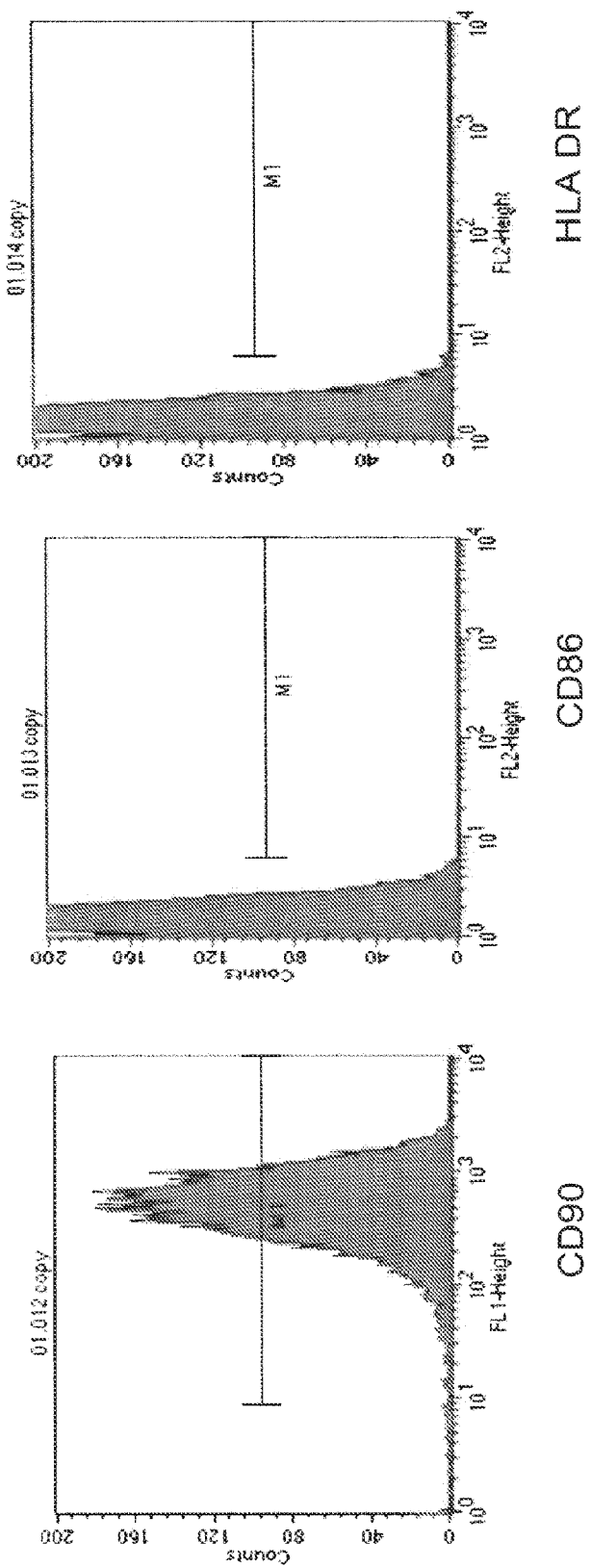
Figure 5C:
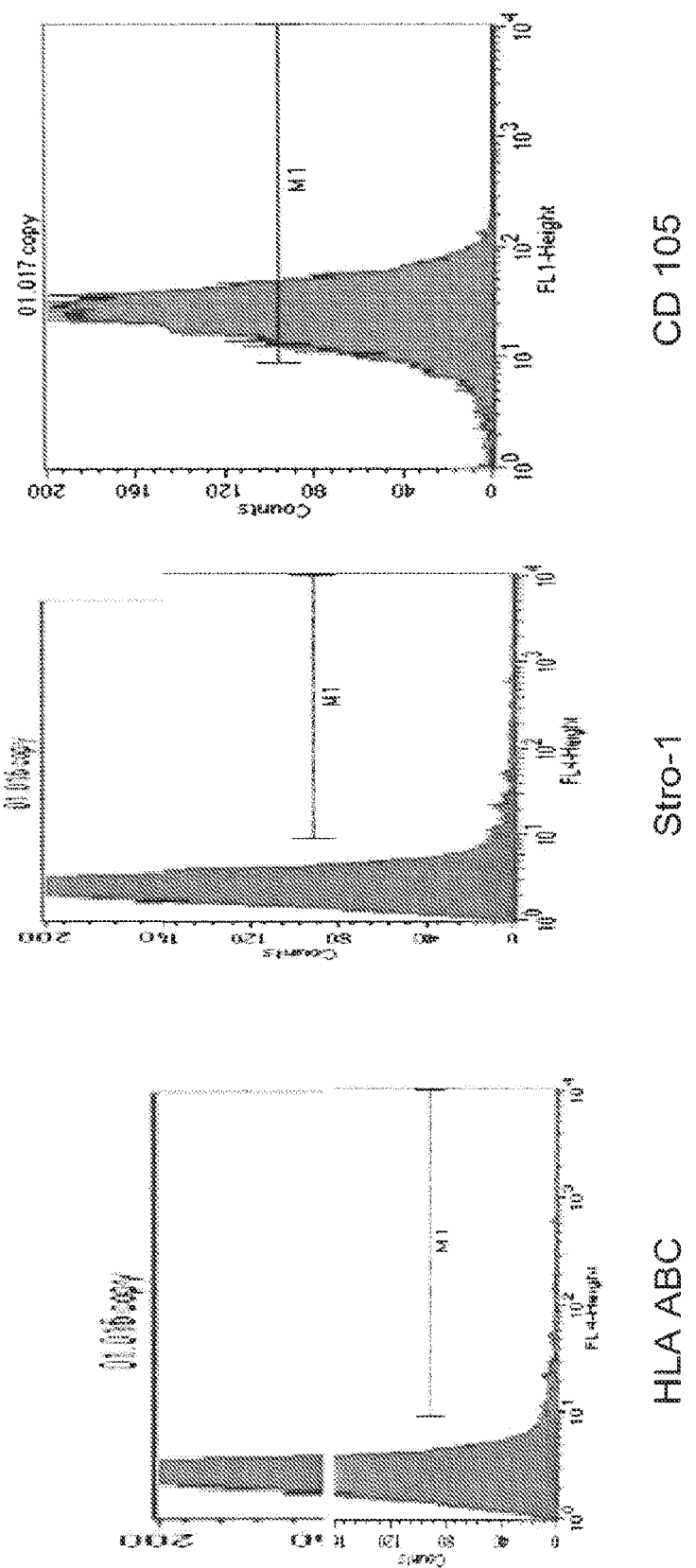
Figure 5D:
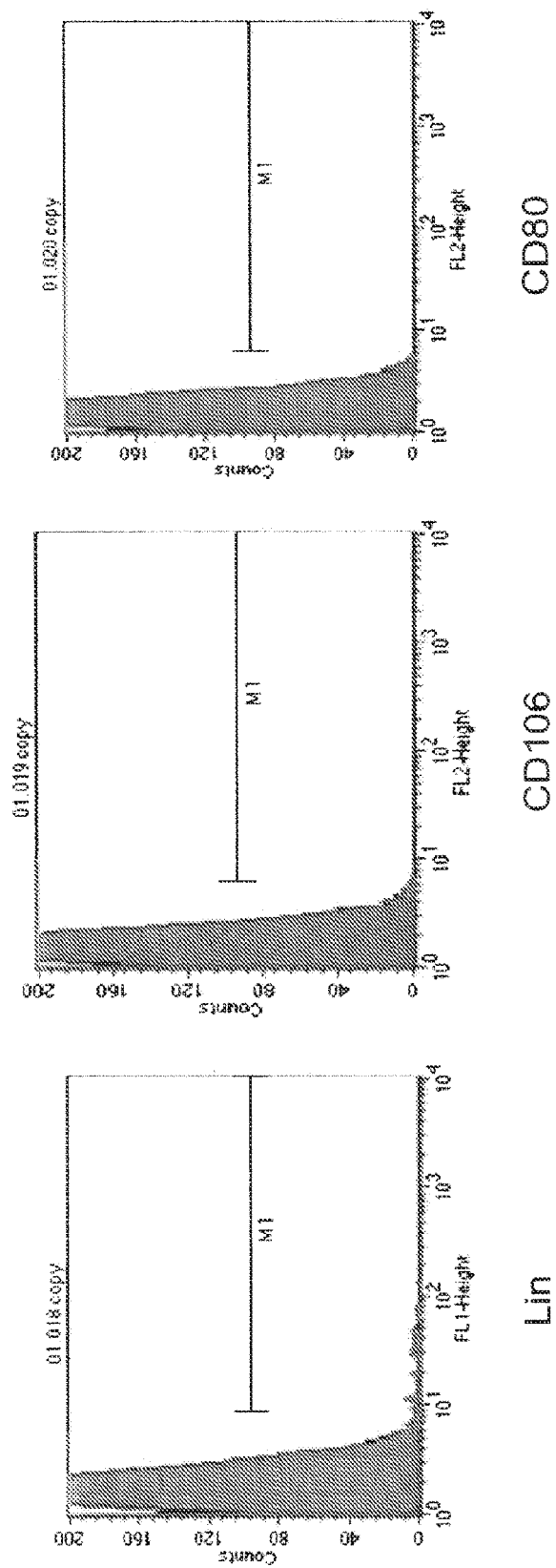
Figure 5E:
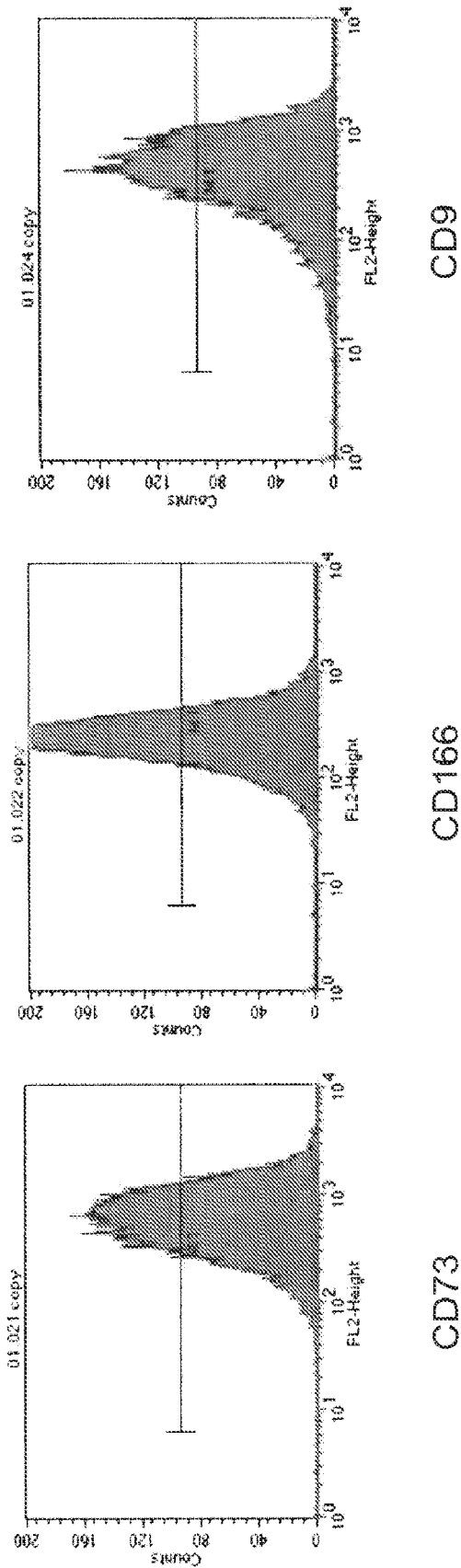
Figure 5F:
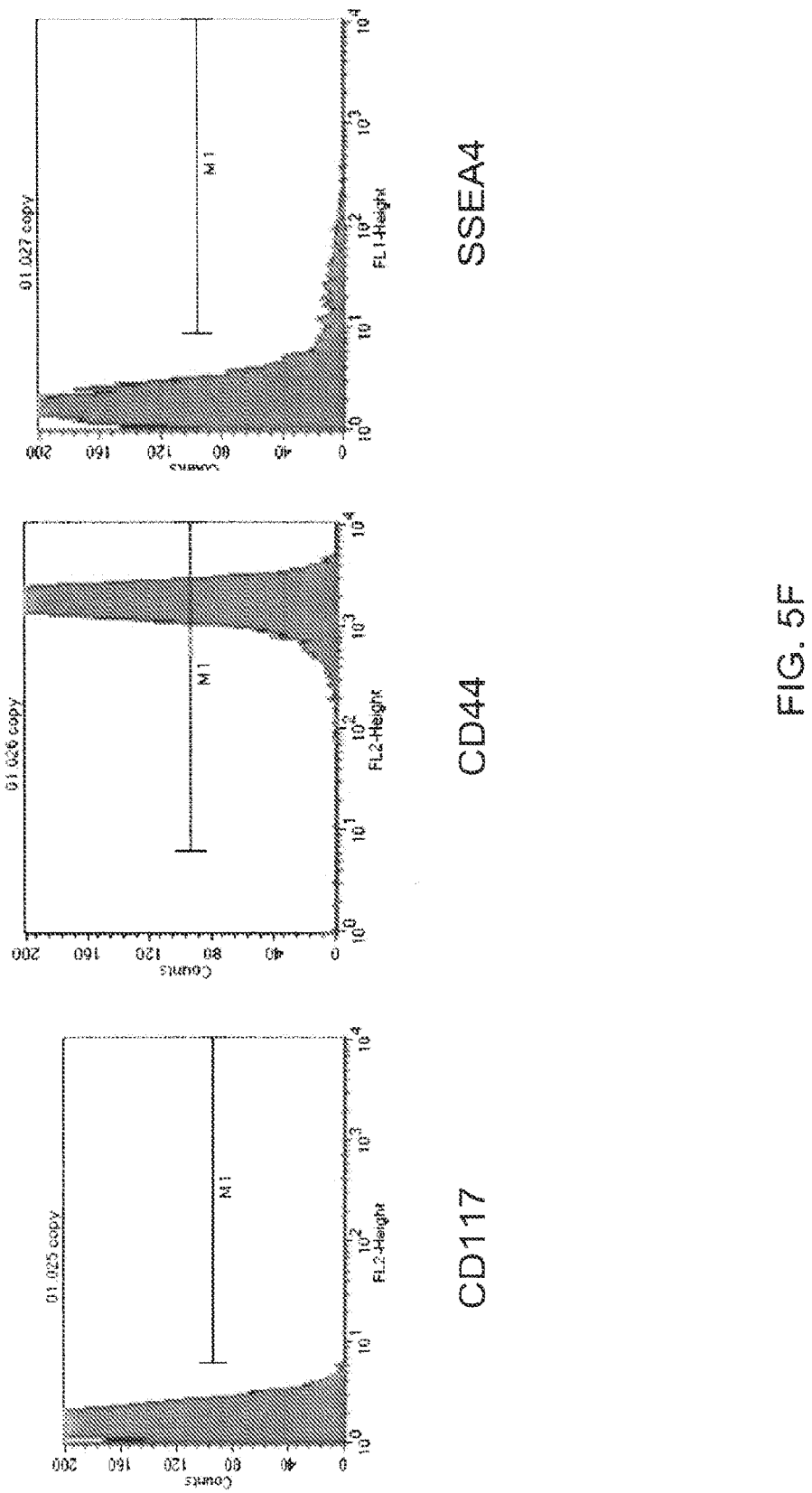
Figure 9:
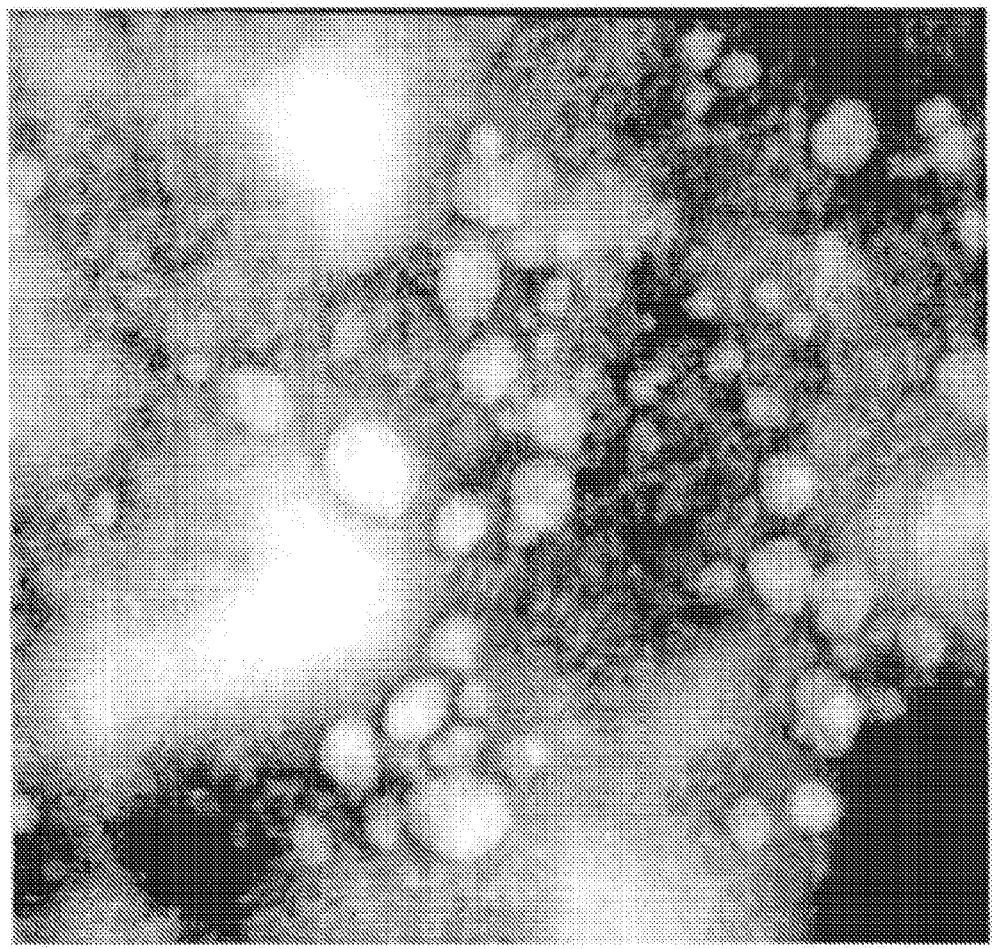
FIG. 9 is a scanning electron micrograph of exosomes isolated from brown fat cells.

Staining of the cells showed that they are positive for the stem cell markers HCAM and CD90 (FIGS. 4 A and B). The expanded cells also expressed exosomes (FIG. 9). Flow cytometry of the cell population demonstrated that the cells were negative for the following cell surface markers: CD34, CD19, CD86, HLA DR, Lin, CD106, CD80, CD 117. The cell population was also low for SSEA4, and Stro-1. The cells were positive for CD63, CD90, HLA ABC, CD 105, CD73, CD 166, CD 9, CD44 (FIGS. 5A-F) which are markers for undifferentiated brown adipose stem cells.

Example 8

Differentiation of Cells into Adipose (White and Brown)

Figure 6:
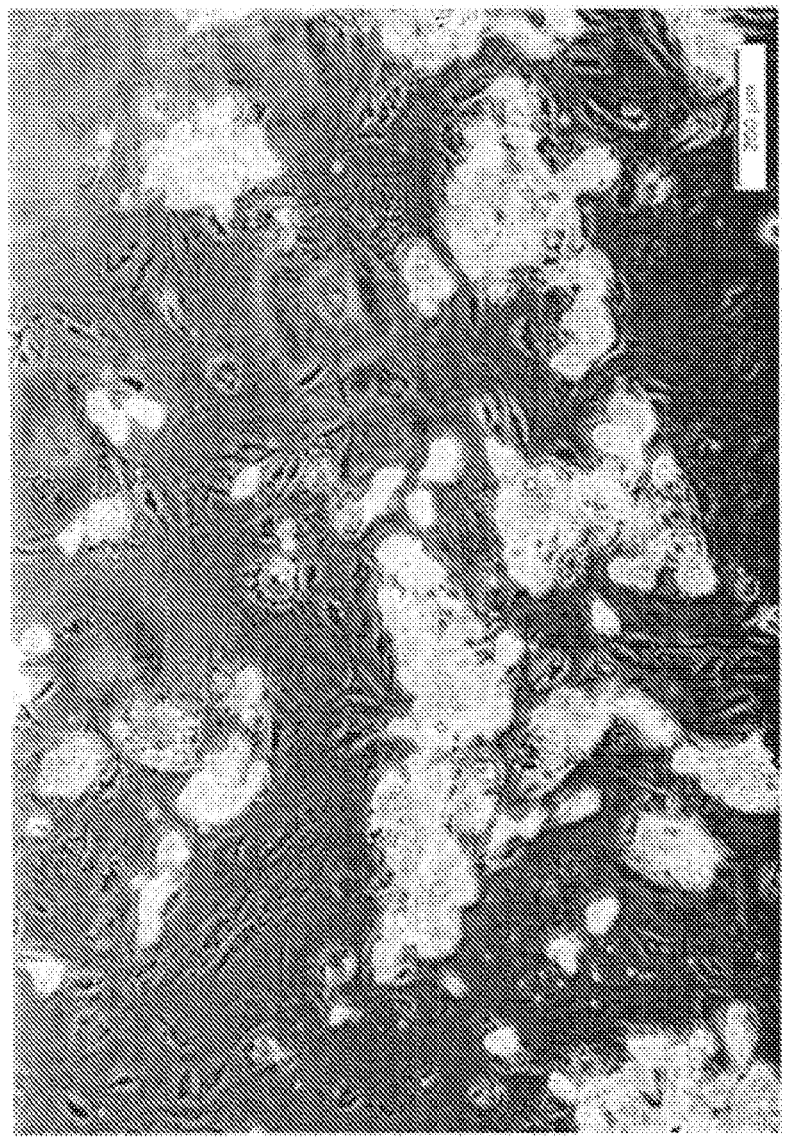
FIG. 6 is a micrograph showing presence of fat droplets in cell culture.

Expanded cells were plated onto cell culture plates and supplemented with adipogenic differentiation medium (Life Technologies). The media was changed every 3 days and differentiation was allowed to continue for 14 days. After 7 days in induction media, fat droplets were visible within the culture (FIG. 6), indicating that the cells had begun differentiating into adipose cells.

Figure 7:
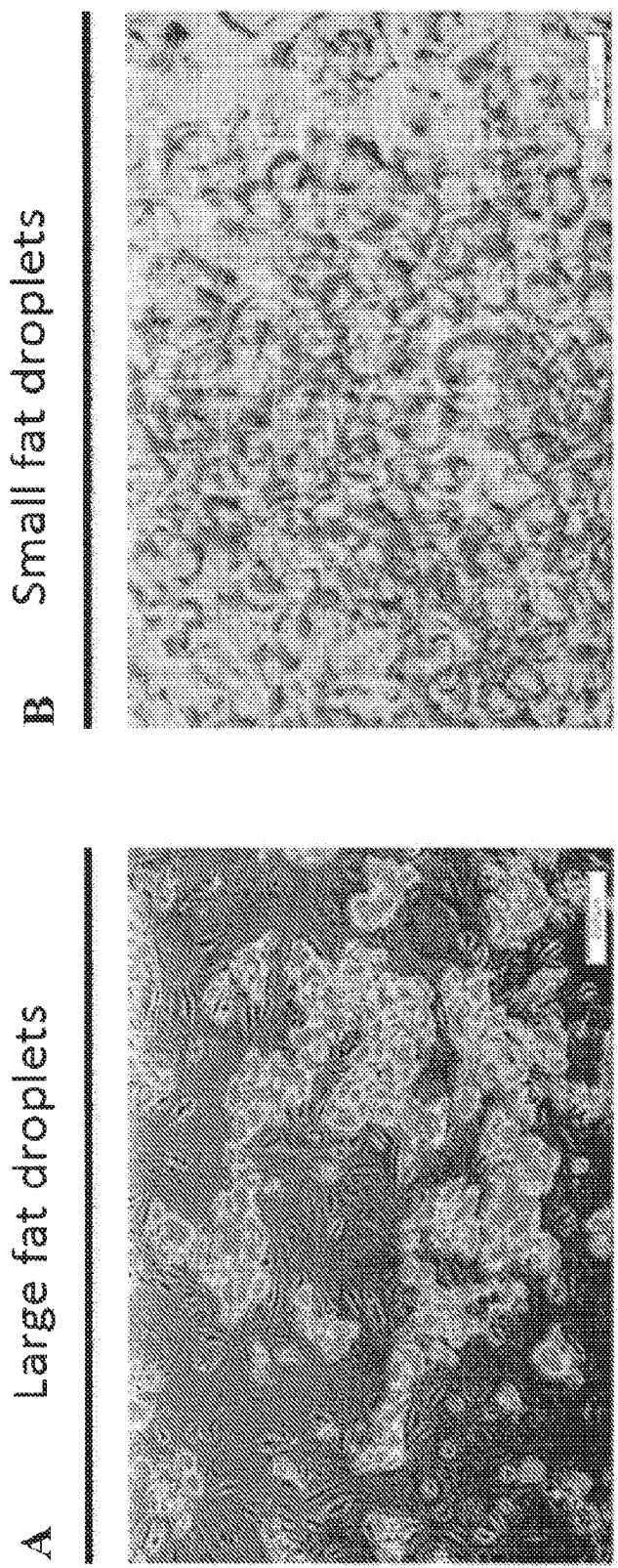

Staining with oil red O demonstrated positive differentiation into adipose cells (FIG. 7).

Identification of positive brown fat droplets in the differentiation was observed by the accumulation of smaller fat droplets (FIG. 7B) compared to those found in cells differentiated from cells derived from white fat depots, which produce larger fat droplets (FIG. 7A).

In another embodiment stem cells were plated in 6-well dishes at a density of 50,000 cells/well. White or brown adipogenesis differentiation medium was added. For brown adipogenesis, FNDC5 was added 6 days post induction as previously described. 0.3% Oil Red O (Sigma Aldrich) was used for staining to detect intracellular lipid accumulation.

Example 9

Chondrogenic and Osteogenic Induction of Cells

Figure 8:
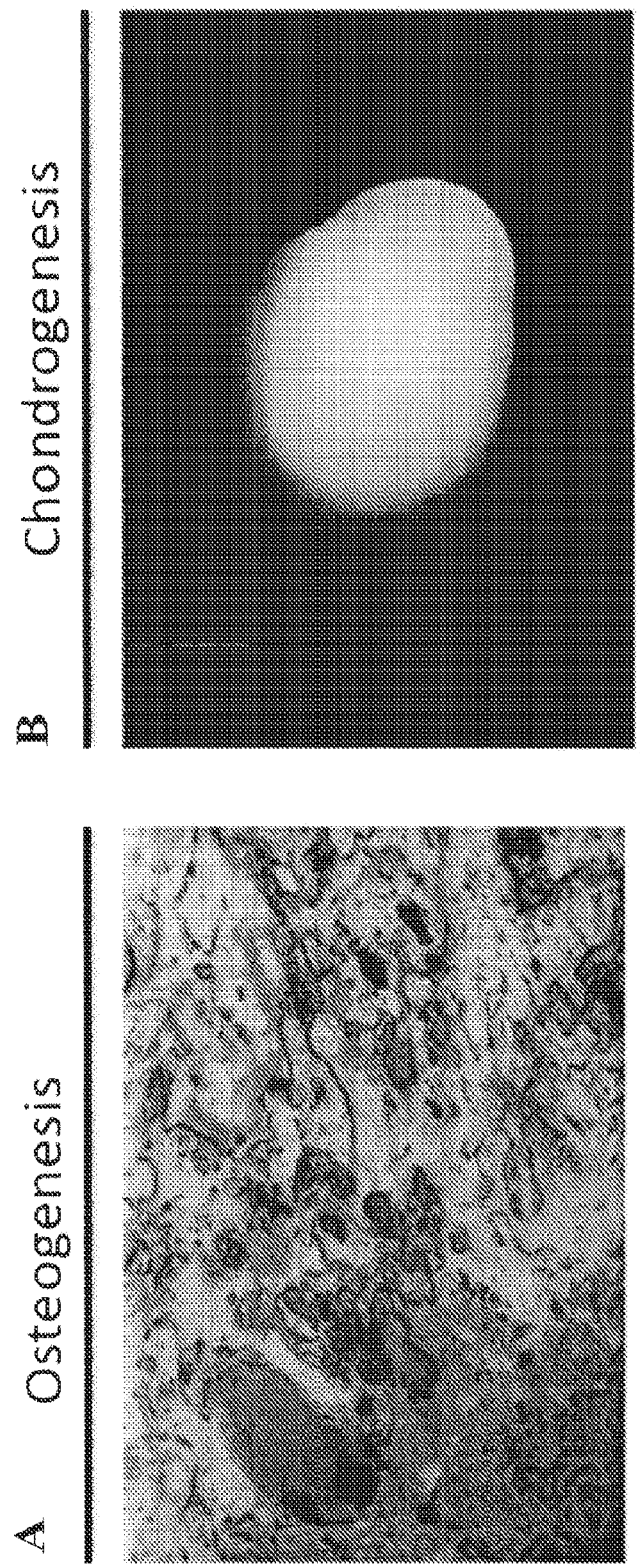
FIGS. 8A and B are micrographs of cells stained with markers of differentiation.
FIG. 8B shows staining with osteocalcin antibody and alcian blue, to show chondrogenesis.

Expanded cells were plated onto cell culture plates and supplemented with osteogenic and chondrogenic medium (Life Technologies). The media was changed every 3 days and differentiation was allowed to continue for 21 days. Confirmation of differentiation into chondroblasts and osteoblasts was observed by staining of the cells with alizarian red or osteocalcin antibody and alcian blue (FIGS. 8 A and B). These data indicate that progenitor cells isolated from brown fat depots maintain the ability to differentiate in to a variety of cell types other than white adipose or brown adipose.

Example 10

Therapeutic Use of Brown Fat Progenitor Cells

NOD-SCID mice are severely immune deficient and are used as a model system to test human cell-based therapies. Mice were raised on high fat/high carbohydrate chow throughout the test period. Mice were split into two groups: 10 untreated mice served as controls and 10 mice received a single subcutaneous injection underneath the dorsal skin of about 1 million human brown fat progenitor cells cultured as described in examples 5-9. The following analytes were measured for four months following injection: plasma glucose, triglycerides, cholesterol, leptin, and adipon. Body weight also was monitored. Baseline is 23+/−5 g in the control group and 25+/−7 g in the treated group. The control group received a sham injection of carrier solution (DPBS) with no cells.

Figure 10:
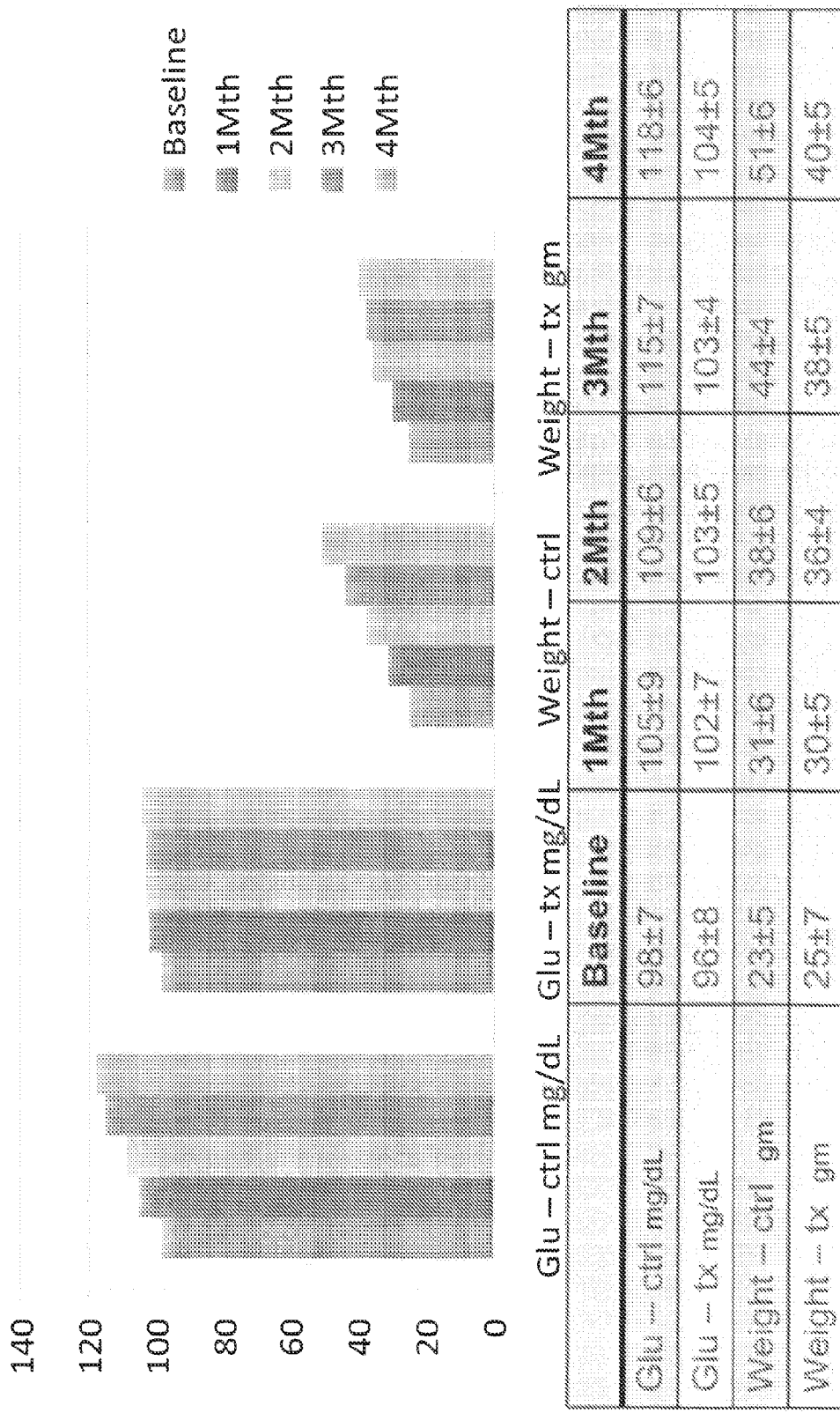
FIG. 10 shows a timecourse of glucose levels and body weight in mice treated with brown fat progenitor cells.
Figure 11:
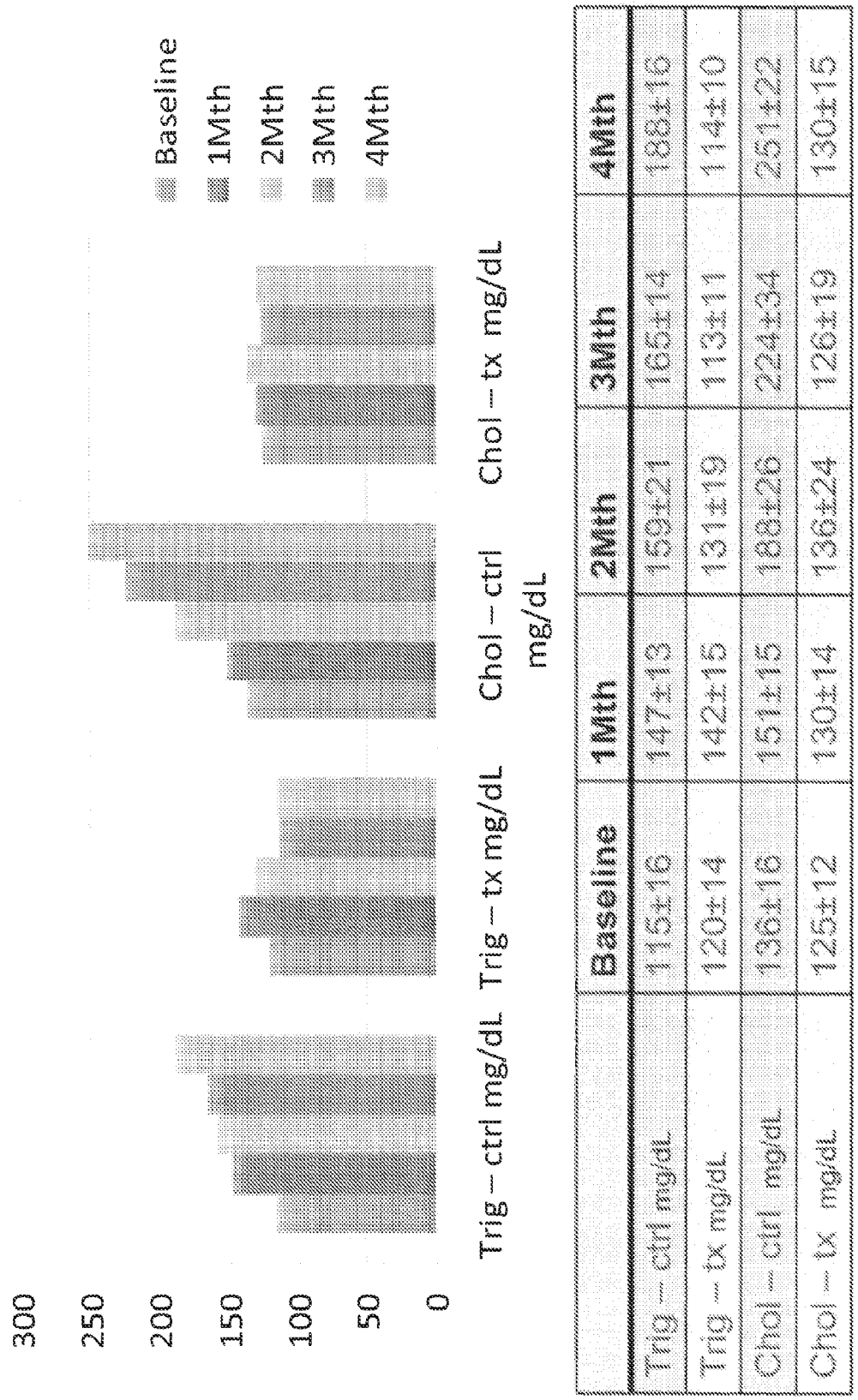
FIG. 11 shows a timecourse of triglyceride levels and cholesterol levels in mice treated with brown fat progenitor cells.
Figure 12:
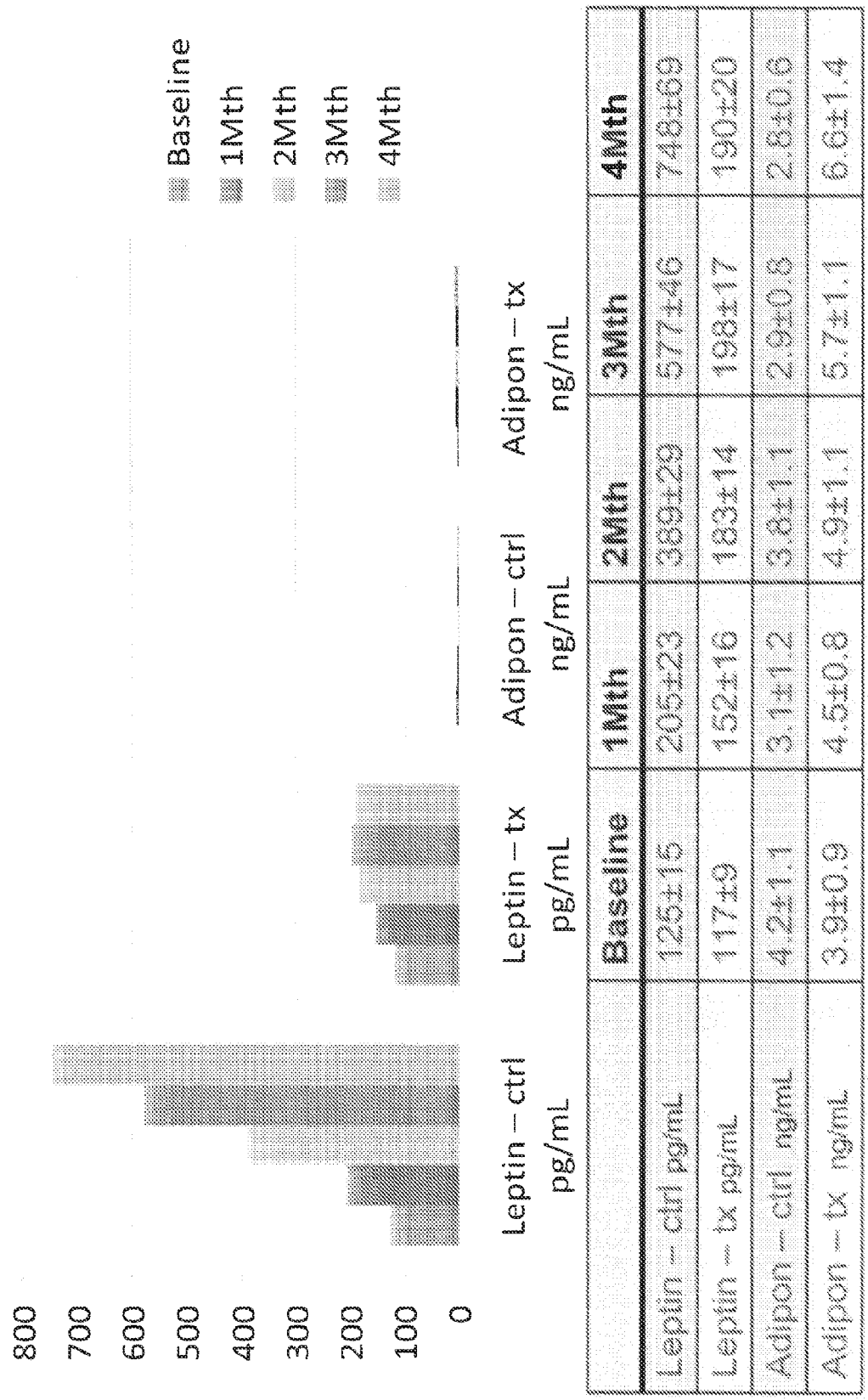
FIG. 12 shows a timecourse of leptin levels and adipon levels in mice treated with brown fat progenitor cells.

Compared to the control group that received a sham injection of carrier solution only (DPBS) with no cells, the experimental cohort which received a dose of 1,000,000 cells demonstrated a decrease in plasma glucose, triglycerides, cholesterol, and weight gain over a four month monitoring period. Adiponectin and leptin levels also correlated to improved levels due to the having received the cell dose. This is in sharp contrast compared to the untreated control mice that received the sham carrier solution (FIGS. 10-12).

Equivalents

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of generating a stem cell, comprising:
    obtaining brown fat tissue;
    isolating a stem cell from the brown fat tissue; and
    culturing the stem cell in a differentiation medium not comprising a xenogenic animal product, wherein the differentiation medium comprises, insulin, dexamethasone, isobutylmethylxanthine, indomethacin, triiodothyronine (T3), rosiglitazone, fibronectin type III domain-containing protein 5 (FNDC5), and 0.5 to 20% human platelet lysate;
    thereby generating a stem cell,
    wherein the stem cell is positive for one or more of the following cell surface markers: CD63, CD90, HLA, ABC, CD105, CD73, CD166, CD9, CD44, and
    wherein the stem cell is negative for one or more of the following cell surface markers: CD34, CD19, CD86, HLA DR, Lin, CD106, CD80, CD117.

2. The method of claim 1, wherein the brown fat tissue is from a sample obtained from a subject.

3. The method of claim 1, wherein the differentiation medium further comprises an anticoagulant selected from a group consisting of heparin and acid-citrate dextrose.

4. The method of claim 1, further comprising cold shocking the stem cell, wherein the cold shocking comprises:
    exposing the stem cell to daily cycles of 4° C. to 25° C. for one hour followed by exposing the stem cell to 37° C.

5. The method of claim 1, further comprising exposing the stem cell in the differentiation medium to hypoxic conditions.

6. The method of claim 1, wherein the differentiation medium comprises 10 to 20% human platelet lysate.

7. A method of generating a stem cell, comprising:
    obtaining brown fat tissue;
    isolating a stem cell from the brown fat tissue; and
    culturing the stem cell in a differentiation medium not comprising a xenogenic animal product, wherein the differentiation medium consists essentially of insulin, dexamethasone, isobutylmethylxanthine, indomethacin, triiodothyronine (T3), rosiglitazone, fibronectin type III domain-containing protein 5 (FNDC5), and 0.5 to 20% human platelet lysate;
    thereby generating a stem cell,
    wherein the stem cell is positive for one or more of the following cell surface markers: CD63, CD90, HLA, ABC, CD105, CD73, CD166, CD9, CD44, and
    wherein the stem cell is negative for one or more of the following cell surface markers: CD34, CD19, CD86, HLA DR, Lin, CD106, CD80, CD117.

8. The method of claim 7, wherein the brown fat tissue is from a sample obtained from a subject.

9. The method of claim 7, further comprising exposing the stem cell in the differentiation medium to hypoxic conditions.

10. The method of claim 7, wherein the differentiation medium comprises 10 to 20% human platelet lysate.

11. A method of generating a stem cell, comprising:
    obtaining brown fat tissue;
    isolating a stem cell from the brown fat tissue; and
    culturing the stem cell in a differentiation medium not comprising a xenogenic animal product, wherein the differentiation medium comprises 0.5 to 20% human platelet lysate;
    cold shocking the stem cell, wherein the cold shocking comprises: exposing the stem cell to daily cycles of 4° C. to 25° C. for one hour followed by exposing the stem cell to 37° C.;
    thereby generating a stem cell;

wherein the stem cell is positive for one or more of the following cell surface markers: CD63, CD90, HLA, ABC, CD105, CD73, CD166, CD9, CD44, and wherein the stem cell is negative for one or more of the following cell surface markers: CD34, CD19, CD86, HLA DR, Lin, CD106, CD80, CD117.

12. The method of claim 11, wherein the differentiation medium further comprises insulin, dexamethasone, isobutyl-methylxanthine, indomethacin, triiodothyronine (T3), rosiglitazone, and fibronectin type III domain-containing protein 5 (FNDC5).

13. The method of claim 11, wherein the differentiation medium further comprises an anticoagulant selected from a group consisting of heparin and acid-citrate dextrose.

14. The method of claim 11, wherein the brown fat tissue is from a sample obtained from a subject.

15. The method of claim 11, further comprising exposing the stem cell in the differentiation medium to hypoxic conditions.

16. The method of claim 11, wherein the differentiation medium comprises 10 to 20% human platelet lysate.

* * * * *